(12) United States Patent
Barker et al.

(10) Patent No.: US 8,182,811 B2
(45) Date of Patent: May 22, 2012

(54) ANTIBODIES TO CXCL13

(75) Inventors: Wendy Barker, Macclesfield (GB); Feenagh Anne Keyes, Cambridge (GB)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 12/631,170

(22) Filed: Dec. 4, 2009

(65) Prior Publication Data

US 2010/0086942 A1 Apr. 8, 2010

Related U.S. Application Data

(63) Continuation of application No. 12/033,145, filed on Feb. 19, 2008, now abandoned.

(60) Provisional application No. 60/890,888, filed on Feb. 21, 2007, provisional application No. 60/908,041, filed on Mar. 26, 2007.

(51) Int. Cl.
*A61K 39/395* (2006.01)
*C12P 21/06* (2006.01)
*C12N 15/00* (2006.01)
*C12N 5/00* (2006.01)
*C07K 16/18* (2006.01)

(52) U.S. Cl. ............... 424/130.1; 435/69.1; 435/320.1; 435/326; 530/387.1; 530/387.3; 530/387.9

(58) Field of Classification Search .................. None
See application file for complete search history.

(56) References Cited

U.S. PATENT DOCUMENTS 5,872,215 A * 2/1999 Osbourne et al. .......... 530/387.3

FOREIGN PATENT DOCUMENTS

| EP | 1 703 282 A1 | 9/2006 |
|----|---|---|
| EP | 1703282 A1 * | 9/2006 |
| WO | WO 96/17868 | 6/1996 |
| WO | WO 96/24668 | 8/1996 |
| WO | WO 96/39522 | 12/1996 |
| WO | WO 98/14477 | 4/1998 |
| WO | WO 99/28468 | 6/1999 |
| WO | WO 2007/122402 | 11/2007 |
| WO | WO 2007/124414 | 11/2007 |

OTHER PUBLICATIONS

Ansel, K. Mark et al., 2000, "A chemokine-driven positive feedback loop organizes lymphoid follicles", Nature, 406:309-314.
Ansel, K. Mark et al., 2002, "CXCL13 Is Required for B1 Cell Horning, Natural Antibody Production, and Body Cavity Immunity", Immunity, 16:67-76.
Edwards, J. et al., 2006, "B-cell targeting in rheumatoid arthritis and other autoimmune diseases", Reviews Immunology, 6:394-403.
Kanbe K. et al., 1999, "A CXC Chemokine Receptor, CXCR5/BLR1, Is a Novel and Specific Coreceptor for Human Immunodeficiency Virus Type 2", Virology, 265:264-273.
Krumbholz, Markus et al., 2006, "Chemokines in multiple sclerosis: CXCL12 and CXCL13 up-regulation is differentially linked to CNS immune cell recruitment", Brain, 129:200-211.
Lisignoli, Gina et al., 2002, "Human Osteoblasts Express Functional CXC Chemokine Receptors 3 and 5; Activation by Their Ligands, CXCL10 and CXCL13, Significantly Induces Alkaline Phosphatase and β-N-Acetylhexosaminidase Release", Journal of Cellular Physiology, 194:71-79.
Meijer, Joost et al., 2006, "The CXCR5 Chemokine Receptor Is Expressed by Carcinoma Cells and Promotes Growth of Colon Carcinoma in the Liver", Cancer Research, 66: 9576-9582.
Rupprecht, T. et al., 2006, "Zyktokin CXCL13 Ein früher Liquormarker für die Neuroborreliose", Nervenarzt, 77:470-473. (English language abstract found within reference at p. 472).
Widney, Daniel P. et al., 2005, "Serum Levels of the Homeostatic B Cell Chemokine, CXCL13, Are Elevated During HIV Infection", Journal of Interferon & Cytokine Research, 25:702-706.
Zheng, Biao et al., 2005, "CXCL13 Neutralization Reduces the Severity of Collagen-Induced Arthritis", Arthritis & Rheumatism, 52(2):620-626.
R&D Systems, Monoclonal anti-human CXCL 13/BLC/BCA-1 antibody, R&D System Data Sheet, Mar. 11, 2006, pp. 1-2 XP002483019.

* cited by examiner

*Primary Examiner* — Marianne P Allen
(74) *Attorney, Agent, or Firm* — MedImmune Limited

(57) ABSTRACT

The present invention relates to binding members, especially antibody molecules, for CXCL13. The binding members are useful for the treatment of disorders associated with CXCL13, including arthritic disorders such as rheumatoid arthritis.

12 Claims, No Drawings

ANTIBODIES TO CXCL13

CROSS-REFERENCE TO RELATED APPLICATIONS

This application is a continuation of U.S. application Ser. No. 12/033,145 filed Feb. 19, 2008, which claims priority under 35 U.S.C. §119(e) to U.S. Provisional Application No. 60/908,041 filed Mar. 26, 2007 and U.S. Provisional Application No. 60/890,888 filed Feb. 21, 2007.

This invention relates to binding members, especially antibody molecules, for CXCL13. The binding members are useful for treatment of disorders associated with CXCL13, including arthritic disorders such as rheumatoid arthritis.

CXCL13 is a potent B cell chemoattractant, which directs naïve B cells into the follicles of secondary lymphoid organs and is constitutively expressed by follicular dendritic cells (FDCs) and stromal cells in the B cell rich areas of secondary lymphoid organs. CXCL13 is also known as B cell-attracting chemokine 1 (BCA-1). CXCL13 signals through its receptor CXCR5. CXCR5 is a seven-transmembrane spanning G protein coupled receptor and is a member of the CXC-chemokine receptor subfamily of the class 1 GPCR family. CXCR5 is expressed at high levels on naïve and activated B cells, including peripheral blood and tonsillar B cells. It is also expressed on a subset of activated peripheral blood CD4+ T cells and the majority of CD4+ cells in secondary lymphoid tissue. CXCL13 is the only known ligand for CXCR5.

CXCL13 plays a role in the development of peripheral lymphoid organs; for example, Ansel et al [1] have shown that mice deficient in CXCL13 have severe defects in peripheral lymph node development. CXCL13 induces membrane lymphotoxin α1β2 expression on naïve B cells recruited into follicles, which promotes the maturation of FDCs and further enhances CXCL13 production [1]. CXCL13-deficient mice, immunised with a T cell-dependent antigen, form germinal centres in lymph nodes and spleen but these are small and have an irregular architecture suggesting CXCL13 is required for the recruitment and correct positioning of B cells within follicles [1].

CXCL13 also has a role in innate immunity; CXCL13-deficient mice lack both peritoneal and pleural cavity B1 cells and are defective in the production of natural antibodies to body cavity bacterial antigens (Ansel, K M. et al. Immunity, 16: 67-76, 2002).

There is evidence for involvement of CXCL13 in a variety of disorders, as discussed elsewhere herein.

CXCL13 binding members have been reported in the art. For example, MAB801 is a commercially available murine anti-human CXCL13 monoclonal antibody (R & D Systems: MAB801). MAB470 is a rat anti-mouse CXCL13 monoclonal.

By utilising appropriately designed selection techniques and assays, we have developed binding members for CXCL13 that inhibit binding of CXCL13 to its target receptor CXCR5.

A binding member of the invention inhibits binding of CXCL13 to the target receptor, CXCR5. Inhibition of binding may be direct inhibition.

Binding members for CXCL13, also referred to as CXCL13-binding members, are described herein. The binding members bind and may neutralise human CXCL13 and non-human primate CXCL13 e.g. cynomolgus CXCL13. Non-human CXCL13 refers to an ortholog of CXCL13 that occurs naturally in a species other than human.

Binding members of the invention are normally specific for CXCL13 over other members of the CXC family of chemokines, including for example, CXCL3, CXCL5, CXCL6, CXCL8, CXCL10 and/or CXCL12 and thus bind CXCL13 selectively. This may be determined or demonstrated for example in a competition assay. For example, a suitable assay is described herein in Example 2.5.

The binding members are useful for inhibiting binding of CXCL13 to CXCR5 in vivo or in vitro, and may be used for treating disorders associated with CXCL13, such as rheumatoid arthritis, as described in detail elsewhere herein.

As described in more detail below, binding members according to the invention have been shown to neutralise CXCL13 with high potency. Neutralisation means inhibition of a biological activity of CXCL13. Binding members of the invention may neutralise one or more activities of CXCL13. The inhibited biological activity is typically CXCL13 binding to a binding partner. For example, the inhibited biological activity may be binding of CXCL13 to CXCR5.

In accordance with the invention, binding of human or non-human CXCL13 to CXCR5 may be inhibited, e.g. a binding member may inhibit binding of non-human primate, such as cynomolgus, CXCL13 to CXCR5. CXCR5 may be human or non-human, such as non-human primate, e.g. cynomolgus, or mouse CXCR5. In one aspect the CXCR5 is of the same species as the CXCL13. Typically CXCR5 is human CXCR5.

Neutralisation of CXCL13 binding to CXCR5 may for example be measured as a function of CXCR5 signalling-mediated activity, since CXCL13 binding to CXCR5 stimulates such activity.

Since CXCR5 is a G-protein coupled receptor, the activity may be an activity associated with G-protein coupled receptors.

For example, binding of CXCL13 to CXCR5 can result in down regulation of adenylyl cyclase activity and a decrease in cellular cAMP levels, through release of the G-protein subunit Gαi, which inhibits adenylyl cyclase. Therefore a suitable assay may comprise detecting an inhibition of the decrease in cellular cAMP levels that occurs in the absence of the binding member i.e. a cAMP assay referred to herein measures the inhibition (by a binding member of the invention) of CXCL13 mediated decreases in cellular cAMP levels. Typically, the cells used in the cAMP assay are co-stimulated with an adenyl cyclase activator, such as NKH477. Suitable cells for use in such an assay are described herein.

Suitable (cellular) cAMP assays include those which combine the techniques of fluorescence resonance energy transfer (FRET) and time resolved fluorescence (TRF) in an homogeneous assay format (a TRF/FRET cAMP assay as referred to herein). Examples of a TRF/FRET cAMP assay include the HTRF® (Homogeneous Time Resolved Fluorescence) cAMP assay (CisBio International) (see, e.g. Gabriel D et al, (2003) Assay and Drug Development Technologies 1(2): 291-303) and the LANCE® cAMP assay (Perkin Elmer) (see, e.g. Hemmila et al (1999) J Biomol Screen 4(6): 303-308).

FRET refers to a non-radiative energy transfer of excitation energy between a donor-fluorophore and a suitable acceptor fluorophore (a FRET donor-acceptor pair). Typically the assay components include: labelled cAMP (tracer cAMP); and labelled cAMP specific antibody. Each of the tracer cAMP and the antibody are labelled with one member of a donor-acceptor pair. When the antibody binds to the tracer cAMP, FRET occurs and the signal emitted by the acceptor is determined by TRF. Free cAMP in a sample competes with the tracer cAMP for binding to antibody and reduces the FRET signal. The assay thus comprises determining the signal emitted by the acceptor.

Preferably the assay comprises determining the specific signal of both the donor and the acceptor as an internal control to give a ratio measurement, which compensates for the presence of coloured compounds in the assay.

In the present assay, the donor acceptor pair is typically such that the donor is excited by a light at about 337 to 340 nm. Typically, following FRET between the donor and the acceptor, the acceptor emits a signal at about 665 nm (which can be time resolved). For example, both XL665 (acceptor in the HTRF® cAMP assay) and the Alexa Fluor®-647 dye (acceptor in the LANCE® cAMP assay) emit a fluorescent signal at 665 nm. A donor may for example emit a signal at about 615 to 620 nm.

An acceptor may be for example, a red-absorbing fluorescent dye, in particular a hydrophilic red-absorbing dye (Buschmann et al, Bioconjugate Chem. 2003, 14: 195-204). A red-absorbing fluorescent dye may be for example, Alexa Fluor®-647 (Perkin Elmer) such as is used in the LANCE® cAMP assay.

Examples of donor-acceptor pairs include the europium cryptate (donor)/XL665 (acceptor), e.g. as used in the HTRF® cAMP assay, and the europium chelate (donor)/Alexa Fluor®-647dye (acceptor), e.g. as used in the LANCE® cAMP assay.

Either the tracer cAMP or the antibody may be labelled with the donor or the acceptor. Thus an assay may comprise use of (donor label-tracer cAMP) and (acceptor label-cAMP specific antibody), or of (acceptor label-tracer cAMP) and (donor label-cAMP specific antibody). For example, an assay may comprise the use of XL665-cAMP and europium cryptate-anti-cAMP monoclonal antibody, e.g. as in the HTRF® assay. An assay may comprise use of europium chelate-labelled cAMP and Alexa Fluor®-647dye labelled cAMP antibody, e.g. as in the LANCE® assay.

Fluorescent signals in a TRF/FRET assay are determined by TRF.

A TRF/FRET cAMP assay can be used to assay inhibition of CXCL13 mediated decreases in cellular cAMP levels upon costimulation of CH0qi5 CXCR5 cells with the adenylyl cyclase activator, NKH477.

In a HTRF® assay generally, macromolecules which may bind to each other are labelled, one with europium (Eu3+) cryptate (donor) and the other with a second fluorescent label, XL665 (or XLent) (a stable cross linked allophycocyanin). When the molecules bind each other, and upon excitation (at 337 nm), FRET occurs and XL665 reemits a specific long-lived fluorescence at 665 nm. In the assay, the specific signals of both the donor (at 620 nm) and the acceptor (at 665 nm) are measured as an internal control, giving a ratio measurement that compensates for the presence of coloured compounds in the assay.

A HTRF® cAMP assay typically comprises: mixing XL665-cAMP (tracer cAMP), europium cryptate-anti-cAMP monoclonal antibody and a sample containing cAMP; applying light at 337 nm (thereby exciting the europium cryptate donor); determining the fluorescent signal at 620 nm (donor) and 665 nm (acceptor) by TRF; and determining the ratio of signal 665 nm/620 nm as a measure of the FRET which has occurred. Any free cAMP from a sample competes with XL665-cAMP (tracer cAMP) for binding to europium cryptate-anti-cAMP monoclonal antibody. Maximum FRET occurs when a sample does not contain any cAMP and the FRET signal decreases with increasing sample cAMP.

The HTRF® technology thus takes advantage of the possibilities offered by fluorescence to work on both the spectral characteristics of the signal emitted (patented ratio correction) and under a time resolved detection mode (eliminating, e.g. auto fluorescence). The technology is homogeneous, which means that samples and detection reagents are mixed together in a plate, which can be read in a suitable plate reader, the so-called "mix and read" protocol.

The LANCE® cAMP assay combines TRF and FRET and also the use of a red-shifted Alexa® Fluor dye (Perkin Elmer), which allows a FRET assay without the compound interference associated with blue dyes.

A LANCE® cAMP assay typically comprises:mixing a europium-chelate of europium/streptavidin-biotin/cAMP tracer, Alexa Fluor®-647-labelled cAMP specific antibody and a sample containing cAMP; applying light at 340 nm (thereby exciting the europium donor); and determining the fluorescent signal at 665 nm (acceptor) by TRF as a measure of the FRET which has occurred. Residual energy from the chelate produces a light at 615 nm. Any free cAMP from a sample competes with europium labelled-cAMP (tracer cAMP) for binding to Alexa®-labelled-anti-cAMP monoclonal antibody. Maximum FRET occurs when a sample does not contain any cAMP and the FRET signal decreases with increasing sample cAMP.

Suitable standards may be used to calibrate the assays.

Assay protocols and examples of performance of these assays are described in detail in the Materials and Methods section herein.

Another CXCR5 signalling-mediated activity, which may be assayed, in order to determine neutralisation of CXCL13 binding to CXCR5 is CXCL13 induced calcium release. Typically a binding member is assayed for an inhibitory effect on CXCL13 induced calcium release in cells expressing CXCR5 and the G-protein Gqi5. Stimulation of these cells with CXCL13 gives rise to increases in cytoplasmic Ca2+ in a concentration dependent manner by inducing release from intracellular stores and influx from extracellular media. This can be measured using calcium sensitive dyes in a Fluorescence Imaging Plate Reader (FLIPR). For example, one such assay uses human CXCL13 and a CHO cell line transfected with Gqi5 and human CXCR5.

cAMP assays and Ca2+ release assays may be performed in vitro with a mammalian cell line, e.g. Chinese Hamster Ovary (CHO) cells such as CHO K1 cells, expressing CXCR5 and the G protein Gqi5 which contains the G$\alpha$i subunit. Suitable cell lines may be produced by transfecting the cells with nucleic acid encoding CXCR5 and Gqi5.

CXCL13 is a potent B cell chemoattractant. CXCL13 signals through the CXCR5 receptor, which is expressed at high levels on naïve and activated B cells, and on a subset of activated T cells. Therefore another activity, which may be assayed, in order to determine neutralisation of CXCL13 binding to CXCR5 is CXCL13 induced chemotaxis in B cells expressing CXCR5.

The B cells in the assay may be non-primary B cells. One such assay uses a murine pre-B cell line that has been transfected with human recombinant CXCR5 (B300.19 hCXCR5 cells).

Alternatively, primary B cells may be used. One such assay uses a mixed lymphocyte population isolated from murine spleen.

Thus, suitable assays, such as the cAMP, calcium release and B cell chemotaxis assays can be used to calculate a binding member's potency for inhibiting binding of CXCL13 to CXCR5, as described below. These assays can be used to calculate potency of a binding member for neutralising CXCL13 binding to CXCR5. The neutralising potency is calculated as a function of the CXCR5 signalling-mediated activity. The assay may measure potency of neutralising CXCL13 induced: decrease in cellular cAMP levels; increase in cellular calcium levels; or B cell chemotaxis.

Inhibition in biological activity may be partial or total. Binding members may inhibit CXCL13 biological activity by 100%, or at least 95%, at least 90%, at least 85%, at least 80%, at least 75%, at least 70%, at least 60%, or at least 50% of the activity in absence of the binding member.

Neutralising potency of a binding member may be determined. Potency is normally expressed as an $IC_{50}$ value, in nM unless otherwise stated. In functional assays, $IC_{50}$ is the concentration of a binding member that reduces a biological response by 50% of its maximum. In ligand-binding studies, $IC_{50}$ is the concentration that reduces receptor binding by 50% of maximal specific binding level. $IC_{50}$ may be calculated by plotting % of maximal biological response as a function of the log of the binding member concentration, and using a software program, such as Prism (GraphPad) to fit a sigmoidal function to the data to generate $IC_{50}$ values. Potency may be determined or measured using one or more assays known to the skilled person and/or as described or referred to herein.

Neutralisation of CXCL13 activity by a binding member in an assay described herein, e.g. a cAMP, calcium release or B cell chemotaxis assay, indicates that the binding member binds CXCL13 and inhibits binding of CXCL13 to CXCR5. Other methods that may be used for determining binding of a binding member to CXCL13 include ELISA, Western blotting, immunoprecipitation, affinity chromatography and biochemical assays.

Neutralising potency of a binding member as calculated in an assay using CXCL13 from a first species (e.g. human) may be compared with neutralising potency of the binding member in the same assay using CXCL13 from a second species (e.g. a non-human primate such as cynomolgus), in order to assess the extent of cross-reactivity of the binding member for CXCL13 of the two species. Alternatively, cross-reactivity may be assessed in a competition binding assay, as described in more detail elsewhere herein.

A binding member of the invention may have a potency for neutralising binding of human CXCL13 to CXCR5 that is within 10-fold of its potency for neutralising binding of cynomolgus CXCL13 to CXCR5. Potency may for example be as measured in a cAMP assay (e.g. a TRF-FRET assay such as a LANCE® cAMP assay) or in a B cell chemotaxis assay, with human and cynomolgus CXCL13 respectively. Potency in the cAMP assay e.g. a LANCE® cAMP assay with human CXCL13 may, for example, be not more than 10-, 5-, 4-, 3- or 2-fold different than in a cAMP assay with cynomolgus CXCL13. Potency in the cAMP assay is as determined for a final concentration of human or cynomolgus CXCL13 of 2 nM. Examples of data obtained in a LANCE® cAMP assay with human CXCL13 and cynomolgus CXCL13 are shown in Tables 2 and 5.

A binding member of the invention may bind human CXCL13 more strongly than cynomolgus CXCL13. The strength of binding of a binding member to human CXCL13 may for example be not more than 10, 9, 8, 7, 6, 5, 4, 3, or 2-fold greater than for cynomolgus CXCL13 as measured in a competition binding assay. For example, the strength of binding may be not more than 4-fold greater for human CXCL13 than for cynomolgus CXCL13. Examples of data obtained in a competition assay with human and cynomolgus CXCL13 are shown in Table 8.

A binding member of the invention may have a neutralising potency or $IC_{50}$ of not more than 12 nM in a human CXCL13 cAMP assay, as described herein, with a 2 nM final concentration of CXCL13. The $IC_{50}$ may for example be not more than 11, 10, 9, 8, 7, 6, 5, 4, 3, 2 or 1 nM, such as not more than 5 nM. The binding member may be in any form described herein, for example, an IgG or scFv or any other suitable form.

A binding member of the invention may have a neutralising potency or $IC_{50}$ of not more than 12 nM in a cynomolgus CXCL13 cAMP assay, as described herein, with a 2 nM final concentration of CXCL13. The $IC_{50}$ may for example be not more than 11, 10, 9, 8, 7, 6, 5, 4, 3, 2 or 1 nM, such as not more than 3 nM. The binding member may be in any form described herein, for example, an IgG or scFv or any other suitable form.

For example, a binding member of the invention may have a neutralising potency or $IC_{50}$ of not more than 12 nM in a human CXCL13 HTRF® cAMP assay with a 2 nM final concentration of CXCL13. The $IC_{50}$ may for example be not more than 11, 10, 9, 8, 7, 6, 5, 4, 3, 2 or 1 nM, such as not more than 5 nM. Examples of data obtained in a human CXCL13 HTRF® cAMP assay are shown in Table 1.

For example, a binding member of the invention may have a neutralising potency or $IC_{50}$ of not more than 12 nM in a cynomolgus CXCL13 HTRF® cAMP assay with a 2 nM final concentration of CXCL13. The $IC_{50}$ may for example be not more than 11, 10, 9, 8, 7, 6, 5, 4, 3, 2 or 1 nM, such as not more than 3 nM. Examples of data obtained in a cynomolgus CXCL13 HTRF® cAMP assay are shown in Table 1.

In one instance, for example where a binding member assayed is in IgG form, the binding member may have a neutralising potency or $IC_{50}$ of not more than 5 nM in a human CXCL13 cAMP assay as described herein with a 2 nM final concentration of CXCL13. The $IC_{50}$ may for example be not more than 4.5, 4, 3.5, 3, 2.5, 2, 1.9, 1.7, 1.5, 1.3, 1.1, 1.0, 0.9, 0.7 or 0.5 nM, such as not more than 1.4 or not more than 1.6 nM.

In one instance, for example where a binding member assayed is in IgG form, the binding member may have a neutralising potency or $IC_{50}$ of not more than 5 nM in a cynomolgus CXCL13 cAMP assay as described herein with a 2 nM final concentration of CXCL13. The $IC_{50}$ may for example be not more than 4.5, 4, 3.5, 3, 2.5, 2, 1.5, 1, 0.5, 0.4 or 0.2 nM, such as not more than 0.3 nM.

For example, a binding member of the invention, e.g. an IgG, may have a neutralising potency or $IC_{50}$ of not more than 5 nM in a human CXCL13 LANCE® cAMP assay with a 2 nM final concentration of CXCL13. The $IC_{50}$ may for example be not more than 4.5, 4, 3.5, 3, 2.5, 2, 1.9, 1.7, 1.5, 1.3, 1.1, 1.0, 0.9, 0.7 or 0.5 nM, such as not more than 1.4 or not more than 1.6 nM. Examples of data obtained in a human CXCL13 LANCE® cAMP assay are shown in Tables 2 and 5.

For example, a binding member of the invention, e.g. an IgG, may have a neutralising potency or $IC_{50}$ of not more than 5 nM in a cynomolgus CXCL13 LANCE® cAMP assay with a 2 nM final concentration of CXCL13. The $IC_{50}$ may for example be not more than 4.5, 4, 3.5, 3, 2.5, 2, 1.5, 1, 0.5, 0.4 or 0.2 nM, such as not more than 0.3 nM. Examples of data obtained in a cynomolgus CXCL13 LANCE® cAMP assay are shown in Tables 2 and 5.

A binding member of the invention may have a neutralising potency or $IC_{50}$ of not more than 40 nM in a human CXCL13 calcium release assay with a 100 nM final concentration of CXCL13. The $IC_{50}$ may for example be not more than 38, 36, 34, 32, 20, 28, 26, 24, 22, 20, 18, 16, 14, 12, 10, 8, 6, 4, or 2 nM. Examples of data obtained in a human CXCL13 calcium release assay are shown in Tables 4 and 7.

A binding member of the invention may have a neutralising potency or $IC_{50}$ of not more than 12 nM in a human CXCL13 B cell chemotaxis assay with a final concentration of human CXCL13 which gives an approximately ED80 response, and a non-primary B cell line that has been transfected with human recombinant CXCR5. The $IC_{50}$ may for example be not more than 11, 10, 9, 8, 7, 6, 5, 4, 3, 2, 1 or 1.5 nM. Typically the assay uses a B cell line, e.g. a murine pre-B cell line that has been transfected with human recombinant CXCR5, such as B300.19 cells expressing human recombinant CXCR5. Examples of data obtained in a human CXCL13 B cell chemotaxis assay with human CXCL13 are shown in Tables 3 and 6.

A binding member of the invention may have a neutralising potency or $IC_{50}$ of not more than 10 nM in a cynomolgus CXCL13 B cell chemotaxis assay with a final concentration of cynomolgus CXCL13 which gives an approximately ED80 response and a non-primary B cell line that has been transfected with human recombinant CXCR5. The $IC_{50}$ may for example be not more than 9, 8, 7, 6, 5, 4, 3, 2 or 1 nM. Typically the assay uses a B cell line, e.g. a murine pre-B cell line that has been transfected with human recombinant CXCR5, such as B300.19 cells expressing recombinant CXCR5. Examples of data obtained in a cynomolgus CXCL13 B cell chemotaxis assay with are shown in Table 6.

A binding member of the invention may have a neutralising potency or $IC_{50}$ of not more than 40 nM in a human CXCL13 primary cell chemotaxis assay with a final concentration of human CXCL13 which gives an approximately ED80 response, and a mixed lymphocyte population. The $IC_{50}$ may for example be not more than 38, 36, 34, 32, 30, 28, 26, 24, 22, 20, 18, 16, 14, 12, 10, 8, 6, 4 or 2 nM. Typically the assay uses a primary lymphocyte population freshly isolated from mouse spleen. An example of data obtained in a human CXCL13 B cell chemotaxis assay with human CXCL13 and murine primary lymphocytes is shown in Table 12.

Binding kinetics and affinity (expressed as the equilibrium dissociation constant $K_D$) of CXCL13 binding members for CXCL13 may be determined, e.g. using surface plasmon resonance e.g. BIAcore. Binding members of the invention normally have an affinity for human CXCL13 of less than 400 pM, for example, less than 380, 360, 340, 320, 300, 290, 280, 270, 260, 250, 240, 230, 220, 210, 200, 190, 180, 170, 160, 150, 140, 130, 120, 110, 100, 90, 80, 70, 60, or 50 pM. Affinity for cynomolgus CXCL13 is normally similar to that for human CXCL13. Examples of data obtained for human CXCL13 and cynomolgus CXCL13 using BIAcore are shown in Tables 10 and 11.

A binding member of the invention may have an affinity for human CXCL-13 and cyno CXCL-13 of less than 150 pM.

Binding kinetics and affinity can be measured using surface plasmon resonance by flowing human or cyno CXCL-13 over a surface comprising the binding member.

In general, and unless otherwise specified, the neutralising potencies described for the assays above may apply to a binding member assayed in any form described herein. For example, the potencies may apply to antibody molecules including any of the antibody fragments described herein, e.g. IgG binding members.

Glycosylated and unglycosylated forms of human CXCL13 were obtained when CXCL13 was expressed recombinantly in mammalian cell lines (MEL cells). The majority of the human CXCL13 produced was unglycosylated, however a smaller fraction containing the glycosylated form could be obtained when expression was scaled-up. Cynomolgus CXCL13 expressed in MEL cells was glycosylated. Potency of antibody 1 for glycosylated and unglycosylated human CXCL13 was within 10-fold different and can be considered equipotent, as measured in the B cell chemotaxis assay described herein. Example potency data for unglycosylated human CXCL13, glycosylated human CXCL13 and glycosylated cynomolgus CXCL13 are shown in Table 6 in Example 2.3. Binding to glycosylated human CXCL13 may represent an advantage of binding members of the invention, since endogenous CXCL13 may be glycosylated and therefore glycosylated human CXCL13 may represent the therapeutic target antigen for human therapy.

In assays described herein, recombinant CXCL13, e.g. human CXCL13, may be used in unglycosylated or glycosylated form. Our data indicate that binding members of the invention may bind an epitope in a region of CXCL13 unaffected by glycosylation (see Example 2.3 and Table 6). Thus, binding member potencies in assays described herein for human CXCL13 may apply both for unglycosylated human CXCL13 and for glycosylated human CXCL13.

A binding member of the invention may have not more than 10-, 5-, 4-, 3-, 2.5-, or 2 fold greater potency for unglycosylated human CXCL13 as compared with glycosylated human CXCL13 in an assay described herein, e.g. the B cell chemotaxis assay. Potency for glycosylated human CXCL13 may of course be greater than potency for unglycosylated human CXCL13.

Potency of binding members of the invention for glycosylated human CXCL13 may be similar or the same as for unglycosylated human CXCL13, e.g. it may be not more than 10-, 5-, 4-, 3-, 2.5- or 2-fold different as measured in a competition binding assay, a cAMP assay, calcium release assay or B cell chemotaxis assay as described herein.

A binding member of the invention may comprise an antibody molecule, e.g. a human antibody molecule. The binding member normally comprises an antibody VH and/or VL domain. VH and VL domains of binding members are also provided as part of the invention. Within each of the VH and VL domains are complementarity determining regions, ("CDRs"), and framework regions, ("FRs"). A VH domain comprises a set of HCDRs, and a VL domain comprises a set of LCDRs. An antibody molecule may comprise an antibody VH domain comprising a VH CDR1, CDR2 and CDR3 and a framework. It may alternatively or also comprise an antibody VL domain comprising a VL CDR1, CDR2 and CDR3 and a framework. Examples of antibody VH and VL domains and CDRs according to the present invention are as listed in the appended sequence listing that forms part of the present disclosure. All VH and VL sequences, CDR sequences, sets of CDRs and sets of HCDRs and sets of LCDRs disclosed herein represent aspects and embodiments of the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs. Typically binding members of the invention are monoclonal antibodies.

A binding member of the invention may comprise an antigen-binding site within a non-antibody molecule, normally provided by one or more CDRs e.g. a set of CDRs in a non-antibody protein scaffold, as discussed further below.

As described in more detail in the Examples, we isolated an antibody molecule, numbered antibody 1. Antibody 1, as described herein, refers to antibodies with the set of CDRs of antibody 1. Sequences for an antibody 1 are shown in the appended Sequence Listing, with the following sequences in the following order: nucleotide sequence encoding VH domain (SEQ ID NO: 1); amino acid sequence of VH domain (SEQ ID NO: 2); VH CDR1 amino acid sequence (SEQ ID NO: 3); VH CDR2 amino acid sequence (SEQ ID NO: 4); VH CDR3 amino acid sequence (SEQ ID NO: 5); nucleotide sequence encoding VL domain (SEQ ID NO: 6); amino acid sequence of VL domain (SE1 ID NO: 7); VL CDR1 amino acid sequence (SEQ ID NO: 8); VL CDR2 amino acid sequence (SEQ ID NO: 9); VL CDR3 amino acid sequence (SEQ ID NO: 10).

A binding member of the invention may comprise one or more CDRs as described herein, e.g. a CDR3, and optionally also a CDR1 and CDR2 to form a set of CDRs. The CDR or set of CDRs may be a CDR or set of CDRs of antibody 1, or may be a variant thereof as described herein.

The invention provides binding members comprising an HCDR1, HCDR2 and/or HCDR3 of antibody 1 and/or an LCDR1, LCDR2 and/or LCDR3 of antibody 1 e.g. a set of CDRs of antibody 1. The binding member may comprise a set of VH CDRs of antibody 1. Optionally it may also comprise a set of VL CDRs of antibody 1, and the VL CDRs may be from the same or a different antibody as the VH CDRs. A VH domain comprising a set of HCDRs of antibody 1, and/or a VL domain comprising a set of LCDRs of antibody 1, are also provided by the invention.

Typically, a VH domain is paired with a VL domain to provide an antibody antigen-binding site, although as discussed further below a VH or VL domain alone may be used to bind antigen. The antibody 1 VH domain may be paired with the antibody 1 VL domain, so that an antibody antigen-binding site is formed comprising both the antibody 1 VH and VL domains. In other embodiments, the antibody 1 VH is paired with a VL domain other than the antibody 1 VL. Light-chain promiscuity is well established in the art. Thus, the VH of antibody 1 may be paired with the VL of antibody 1 or of another antibody.

A binding member may comprise a set of H and/or L CDRs of antibody 1 with one or more amino acid mutations within the disclosed set of H and/or L CDRs. The mutation may be an amino acid substitution, insertion or deletion. Thus for example, there may be up to 10, 9, 8, 7, 6, 5, 4, 3 or 2 mutations, e.g. substitutions, within the set of H and/or L CDRs. For example, there may be one or up to 5, 4, 3 or 2 mutations, e.g. substitutions in HCDR3 and/or there may be one or up to 5, 4, 3 or 2 mutations, e.g. substitutions, in LCDR3.

A binding member may comprise an antibody molecule having one or more CDRs, e.g. a set of CDRs, within an antibody framework. For example, one or more CDRs or a set of CDRs of an antibody may be grafted into a framework (e.g. human framework) to provide an antibody molecule. The framework regions may be of human germline gene segment sequences. Thus, the framework may be germlined, whereby one or more residues within the framework are changed to match the residues at the equivalent position in the most similar human germline framework. A binding member of the invention may be an isolated human antibody molecule having a VH domain comprising a set of HCDRs in a human germline framework, e.g. human germline framework, e.g. human VH3-23. Normally the binding member also has a VL domain comprising a set of LCDRs, e.g. in a human germline framework, e.g. human VK1 L12. A germlined VH or VL domain may or may not be germlined at one or more Vernier residues.

A non-germlined antibody molecule has the same CDRs, but different frameworks, compared to a germlined antibody molecule. The antibody sequences for antibody 1 shown herein in the appended sequence listing, are germlined. As described herein in the Examples, germlining from antibody 1 VH and VL domains as isolated involved making the following mutations in the VH domain: Q1E, V5L, R16G, V23A, G24A, H39Q, G83R and R105Q; and the following mutations in the VL domain: I15V, A58V and D70E. Therefore in one aspect, a VH domain according to the invention (including a binding member comprising such a VH domain) may comprise the amino acid sequence in SEQ ID NO:2 but with 1 or more, e.g. 2, 3, 4, 5, 6, 7 or all 8, of the above VH mutations reversed. In one embodiment, the VH domain is not substituted at positions 30, 97 and 98 of SEQ ID NO. 2. Similarly, a VL domain according to the invention may comprise the amino acid sequence in SEQ ID NO: 7 but with 1, 2, or all 3 of the above VL mutations reversed. In one embodiment, the VL domain is not substituted at position 2 of SEQ ID NO. 7.

In one aspect, a binding member of the invention may comprise (i) a VH domain comprising the amino acid sequence SEQ ID NO:2 or the amino acid sequence SEQ ID NO:2 with one or more amino acid alterations (e.g. substitutions) in one or more of the framework regions (e.g. 1, 2, 3, 4, 5, 6, 7, or 8 substitutions); and (ii) a VL domain comprising the amino acid sequence in SEQ ID NO:7 or the amino acid sequence SEQ ID NO:7 but with one or more amino acid alterations (e.g. substitutions) in one or more of the framework regions (e.g. 1, 2 or 3 substitutions). In one embodiment of this aspect, the VH domain of the binding member (e.g. IgG) is not substituted at one or all of positions 30, 97 and 98 of SEQ ID NO. 2 and the VL domain is not substituted at position 2 of SEQ ID NO:7. The VH domain may comprise the amino acid sequence in SEQ ID NO:2 or may comprise the amino acid sequence in SEQ ID NO:2 with one or more (e.g. 1, 2 or all) of the following amino acid substitutions: G30S; T97A; R98K. The VL domain may comprise the amino acid sequence in SEQ ID NO:7 or may comprise the amino acid sequence in SEQ ID NO:2 with the following amino acid substitution: T2Ile.

Data provided herein for antibody 1 is shown for the germlined and/or non-germlined formats, and this is indicated where appropriate. For antibody that was tested in germlined form, very similar data was obtained compared with the non-germlined form.

The 3' cgt codon, and corresponding Arginine residue, shown in the nucleotide and amino acid sequence for the kappa VL domain of Antibody 1 was included in the expressed scFv and IgG sequences of this antibody. The C terminal Arginine residue of the sequence corresponds to Kabat residue 108. The origin of this residue and its encoding triplet cgt is explained below.

To express the light chain of the IgG, a nucleotide sequence encoding the antibody light chain was provided, comprising a first exon encoding the VL domain, a second exon encoding the CL domain, and an intron separating the first exon and the second exon. Under normal circumstances, the intron is spliced out by cellular mRNA processing machinery, joining the 3' end of the first exon to the 5' end of the second exon. Thus, when DNA having the said nucleotide sequence was expressed as RNA, the first and second exons were spliced together. Translation of the spliced RNA produces a polypeptide comprising the VL domain and CL domain. After splicing, the Arg at Kabat residue 108 is encoded by the last base (c) of the VL domain framework 4 sequence and the first two bases (gt) of the CL domain.

The Arginine residue at Kabat residue 108 may be considered to be the C terminal residue of the VL domain of the antibody molecule.

A binding member of the invention may be one which competes for binding to CXCL13 with any binding member which
(i) binds CXCL13 and
(ii) comprises a binding member, VH and/or VL domain, CDR e.g. HCDR3, and/or set of CDRs disclosed herein.

In one aspect the invention provides a binding member which competes for binding with an scFv antibody molecule having SEQ ID NO: 11. The sequence in SEQ ID NO: 11 corresponds to the VH domain of SEQ ID NO:2 linked to the VL domain of SEQ ID NO:7 by a linker sequence (Gly120 to Ser134). The binding member may comprise a CDR or set of CDRs of antibody 1, or a variant thereof as described elsewhere herein. The binding member may be an antibody molecule e.g. an IgG (e.g. IgG1) or scFv, as described elsewhere herein.

A binding member may show complete or partial competition in a competition assay. For example, a binding member may show at least 50, 55, 60, 65, 70, 75, 80, 85, 90, 95, 97, 99 or 100% competition for binding to CXCL13 in a competition assay, for example, with an antibody scFv molecule having the sequence of SEQ ID NO: 11.

Competition between binding members may be assayed easily in vitro, for example using ELISA and/or by tagging a specific reporter molecule to one binding member which can be detected in the presence of one or more other untagged binding members, to enable identification of binding members which bind the same epitope or an overlapping epitope. Such methods are readily known to one of ordinary skill in the art, and are described in more detail herein. For example, an epitope competition assay using the TRF-FRET technology described herein in relation to cAMP assays, may be used (a TRF-FRET epitope competition assay), e.g. the HTRF® epitope competition assay.

The HTRF® technology is as described herein in relation to cAMP assays. A HTRF® epitope competition assay typically comprises: mixing XL665-labelled CXCL13, europium cryptate-labelled reference antibody (e.g. an scFv antibody molecule having SEQ ID NO: 11) and a test binding member; applying light at 337 nm (thereby exciting the europium cryptate donor); determining the fluorescent signal at 620 nm (donor) and 665 nm (acceptor) by TRF; and determining the ratio of signal 665 nm/620 nm as a measure of the FRET which has occurred. A test binding member, e.g. IgG or ScFv antibody molecule, which competes with the reference antibody for binding to CXCL13 reduces the FRET which occurs. A detailed method for this assay is provided in the Examples.

Thus, a further aspect of the present invention provides a binding member comprising a human antibody antigen-binding site that competes with an antibody molecule, for example especially an antibody molecule comprising a VH and/or VL domain, CDR e.g. HCDR3, or set of CDRs of antibody 1 for binding to CXCL13.

In further aspects the present invention provides a binding member comprising a human antibody antigen-binding site which competes with an antibody antigen-binding site for binding to CXCL13, wherein the antibody antigen-binding site is composed of a VH domain and a VL domain, and wherein the VH and VL domains comprise a set of CDRs of antibody 1 disclosed herein.

A binding member of the invention may bind an epitope of human CXCL-13 wherein said epitope includes at least one residue of the sequence Ile-Leu-Pro-Arg-Gly-Asn-Gly-Cys-Pro-Arg-Lys-Glu (SEQ ID NO: 20) at positions 31-42 of mature human IL-17A. It may for example bind one, two, three, four, five or more than five residues of SEQ ID NO: 20. A binding member of the invention may bind other regions of human CXCL-13 in addition to SEQ ID NO: 20.

Any suitable method may be used to determine the sequence of residues bound by a binding member, e.g. hydrogen-deuterium exchange, site-directed mutagenesis, mass spectrometry, NMR and X-ray crystallography.

Peptide amide hydrogen exchange is a very well described methodology used to study proteins (Englander, S. W. et al. Methods Enzymol. 232:26-42, 1994). More recently this has been further developed to use deuterium labelled proteins that can exchange for protons and coupling this to mass spectrometry to measure the rates of exchange across a whole protein (Pantazatos, D. et al. Proc. Natl. Acad. Sci. 101(3):751-756, 2004). This rate of hydrogen/deuterium exchange (H/D exchange) can be modified significantly by accessibility to solvent such that when a part of the protein is involved in binding to another molecule the rate of exchange will slow significantly. This approach has been used to map the regions of a protein involved in interacting with antibodies, and was used to investigate regions of CXCL-13 involved in binding antibodies of the invention, as detailed in Example 7 herein. Mass spectrometry was used in conjunction with H/D exchange, to identify regions of human CXCL-13 in contact with a binding member. It may be demonstrated for example that H/D exchange for residues within SEQ ID NO: 20 is significantly slowed when human CXCL-13 is bound to a binding member of the invention.

In further aspects, the invention provides an isolated nucleic acid which comprises a sequence encoding a binding member, VH domain and/or VL domain according to the present invention, and methods of preparing a binding member, a VH domain and/or a VL domain of the invention, which comprise expressing said nucleic acid under conditions to bring about production of said binding member, VH domain and/or VL domain, and recovering it.

Another aspect of the present invention provides nucleic acid, generally isolated, encoding a VH CDR or VL CDR sequence disclosed herein.

A further aspect provides a host cell containing or transformed with nucleic acid of the invention.

Further aspects of the present invention provide for compositions containing binding members of the invention, and their use in methods of inhibiting and/or neutralising CXCL13, including methods of treatment of the human or animal body by therapy.

Binding members according to the invention may be used in a method of treatment or diagnosis, such as a method of treatment (which may include prophylactic treatment) of a disease or disorder in the human or animal body (e.g. in a human patient), which comprises administering to said patient an effective amount of a binding member of the invention. Conditions treatable in accordance with the present invention include any in which CXCL13 plays a role, as discussed in detail elsewhere herein.

These and other aspects of the invention are described in further detail below.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

CXCL13

CXCL13 is chemokine (C—X—C motif) ligand 13. A sequence of full length human CXCL13 is deposited under Accession number NP_006410 SEQ ID NO: 12. The full length amino acid sequence includes a 22 residue N-terminal peptide which is cleaved in vivo to generate the mature form. Mature CXCL13 has amino acid sequence SEQ ID NO: 13. Mature CXCL13 is the in vivo target antigen for therapeutic and diagnostic applications, and references herein to human CXCL13 are to mature CXCL13 unless otherwise specified.

For certain assays and experiments described herein, human CXCL13 was expressed in the MEL cell line. Human CXCL13 expressed from MEL cells was truncated at the C-terminus, and its amino acid sequence is SEQ ID NO: 14. Thus, SEQ ID NO: 14 is the MEL-expressed human CXCL13 as used in the assays described herein. Mature, non-truncated CXCL13 (SEQ ID NO: 13) would also be suitable for use in assays and the truncation is not believed to affect the results obtained.

Biotinylated human CXCL13 was used in some of the assays described herein. This CXCL13 was synthetically produced and has the mature CXCL13 sequence SEQ ID NO: 13, carrying biotin at the most C terminal lysine residue.

In some embodiments CXCL13 may be cynomolgus CXCL13. When expressed from MEL cells for the experimental work herein, the cynomolgus CXCL13 was C-terminally truncated by 5 amino acids and has amino acid sequence SEQ ID NO: 16.

A proposed sequence of mature untruncated cynomolgus CXCL13 is SEQ ID NO 15. As shown the full untruncated cyno sequence is proposed to include KRKIP at the C-terminus as for human and rhesus CXCL13. This is assumed because the rhesus primer used for cloning was designed to anneal to the region that is removed from the mature human CXCL13 when it is truncated.

Mature, non-truncated CXCL13 (SEQ ID NO: 15) would also be suitable for use in assays and the truncation is not believed to affect the results obtained.

As described elsewhere herein, CXCL13 may be recombinant, and/or may be either glycosylated or unglycosylated. Glycosylated and/or unglycosylated CXCL13 may be expressed in recombinant systems, e.g. in mammalian cells such as human cell lines, murine cell lines e.g. MEL cells, or in Chinese hamster ovary (CHO) cells.

CXCR5

CXCR5 is the receptor for CXCL13 as described elsewhere herein. Human CXCR5 exists in two isoforms. An amino acid sequence of CXCR5 isoform 1 is deposited under Accession number NP_001707 and is shown herein as SEQ ID NO: 17. An amino acid sequence of CXCR5 isoform 2 is deposited under Accession number NP_116743 and is shown herein as SEQ ID NO: 18. Isoform 2 is truncated by 45 amino acids at the N-terminus. Isoform 2 therefore lacks the translation initiation codon and extracellular domain of variant 1 and is not likely to bind ligand and be functional Isoform 1 of human CXCR5, having SEQ ID NO: 17, was used in the experiments herein. Accordingly, references herein to CXCR5 are to human isoform 1 unless otherwise indicated.

CXCR5 referred to herein may be human or non-human as indicated by the context. For example, in neutralisation assays using human CXCL13 or non-human CXCL13, CXCR5 from an appropriate species may be selected. An appropriate species may be human or non-human CXCR5 where the binding partner is human or non-human CXCL13 from the same species. Alternatively, human or non-human CXCL13 may be used in assays with human or non-human CXCR5 from a different species where human or non-human CXCL13 is known to cross-react.

Binding Member

This describes one member of a pair of molecules that bind one another. The members of a binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, biotin-avidin, hormone-hormone receptor, receptor-ligand, and enzyme-substrate. The present invention is concerned with antigen-antibody type reactions.

A binding member normally comprises a molecule having an antigen-binding site. For example, a binding member may be an antibody molecule or a non-antibody protein that comprises an antigen-binding site.

An antigen-binding site may be provided by means of arrangement of CDRs on non-antibody protein scaffolds, such as fibronectin or cytochrome B etc. [2, 3, 4], or by randomising or mutating amino acid residues of a loop within a protein scaffold to confer binding specificity for a desired target. Scaffolds for engineering novel binding sites in proteins have been reviewed in detail by Nygren et al. [4]. Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004 [5]. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from S. aureus, transferrin, tetranectin, fibronectin (e.g. 10th fibronectin type III domain), lipocalins as well as gamma-crystalline and other Affilin™ scaffolds (Scil Proteins). Examples of other approaches include synthetic "Microbodies" based on cyclotides—small proteins having intra-molecular disulphide bonds, Microproteins (Versabodies™, Amunix) and ankyrin repeat proteins (DARPins, Molecular Partners).

In addition to antibody sequences and/or an antigen-binding site, a binding member according to the present invention may comprise other amino acids, e.g. forming a peptide or polypeptide, such as a folded domain, or to impart to the molecule another functional characteristic in addition to ability to bind antigen. Binding members of the invention may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen-binding site binds to the antigen and thus targets the catalytic site to the antigen. The catalytic site may inhibit biological function of the antigen, e.g. by cleavage.

Although, as noted, CDRs can be carried by non-antibody scaffolds, the structure for carrying a CDR or a set of CDRs of the invention will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat, et al., 1987 [6] and updates thereof. A number of academic and commercial on-line resources are available to query this database. For example, see ref. [7] and the associated on-line resource, currently at the web address of http://www.bioinf.org.uk/abs/simkab.html.

By CDR region or CDR, it is intended to indicate the hypervariable regions of the heavy and light chains of the immunoglobulin as defined by Kabat et al. 1991 [8], and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody [9, 10, 11, 12, 13, 14, 15, 16].

Antibody Molecule

This describes an immunoglobulin whether natural or partly or wholly synthetically produced. The term also covers any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described later. Antibody fragments that comprise an antibody antigen-binding site include, but are not limited to, molecules such as Fab, Fab', Fab'-SH, scFv, Fv, dAb and Fd. Various other antibody molecules including one or more antibody antigen-binding sites have been engineered, including for example $Fab_2$, $Fab_3$, diabodies, triabodies, tetrabodies and minibodies. Antibody molecules and methods for their construction and use are described in [17].

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. For example, human hybridomas can be made as described by Kontermann & Dubel [18]. Phage display, another established technique for generating binding members has been described in detail in many publications, such as Kontermann & Dubel [18] and WO92/01047 (discussed further below), and U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160, 6,521,404.

Transgenic mice in which the mouse antibody genes are inactivated and functionally replaced with human antibody genes while leaving intact other components of the mouse immune system, can be used for isolating human antibodies [19]. Humanised antibodies can be produced using techniques known in the art such as those disclosed in for example WO91/09967, U.S. Pat. No. 5,585,089, EP592106, U.S. Pat. No. 565,332 and WO93/17105. Further, WO2004/006955 describes methods for humanising antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO2004/006955, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies. Chimeric antibodies made according to the method are also disclosed.

Synthetic antibody molecules may be created by expression from genes generated by means of oligonucleotides synthesized and assembled within suitable expression vectors, for example as described by Knappik et al. [20] or Krebs et al. [21].

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment [22, 23, 24], which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen-binding site [25, 26]; (viii) bispecific single chain Fv dimers (PCT/US92/09965) and (ix) "diabodies", multivalent or multispecific fragments constructed by gene fusion (WO94/13804; [27]). Fv, scFv or diabody molecules may be stabilized by the incorporation of disulphide bridges linking the VH and VL domains [28]. Minibodies comprising a scFv joined to a CH3 domain may also be made [29]. Other examples of binding fragments are Fab', which differs from Fab fragments by the addition of a few residues at the carboxyl terminus of the heavy chain CH1 domain, including one or more cysteines from the antibody hinge region, and Fab'—SH, which is a Fab' fragment in which the cysteine residue(s) of the constant domains bear a free thiol group.

Antibody fragments of the invention can be obtained starting from antibody molecule 1, by methods such as digestion by enzymes e.g. pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers, such as those supplied by the company Applied Biosystems, etc., or by nucleic acid synthesis and expression.

Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain [24]. VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. Camelid VH dAbs are being developed for therapeutic use under the name "nanobodies™". A binding member of the present invention may be a dAb comprising a VH or VL domain substantially as set out herein, or a VH or VL domain comprising a set of CDRs substantially as set out herein.

Bispecific or bifunctional antibodies form a second generation of monoclonal antibodies in which two different variable regions are combined in the same molecule [30]. Their use has been demonstrated both in the diagnostic field and in the therapy field from their capacity to recruit new effector functions or to target several molecules on the surface of tumour cells. Where bispecific antibodies are to be used, these may be conventional bispecific antibodies, which can be manufactured in a variety of ways [31], e.g. prepared chemically or from hybrid hybridomas, or may be any of the bispecific antibody fragments mentioned above. These antibodies can be obtained by chemical methods [32,33] or somatic methods [34, 35] but likewise and preferentially by genetic engineering techniques which allow the heterodimerization to be forced and thus facilitate the process of purification of the antibody sought [36]. Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies. Bispecific diabodies, as opposed to bispecific whole antibodies, may also be particularly useful because they can be readily constructed and expressed in E.coli. Diabodies (and many other polypeptides, such as antibody fragments) of appropriate binding specificities can be readily selected using phage display (WO94/13804) from libraries. If one arm of the diabody is to be kept constant, for instance, with a specificity directed against CXCL13, then a library can be made where the other arm is varied and an antibody of appropriate specificity selected. Bispecific whole antibodies may be made by alternative engineering methods as described in Ridgeway et al., 1996 [37].

Various methods are available in the art for obtaining antibodies against CXCL13. The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" [38] or to the technique of preparation from hybridomas described by Köhler and Milstein [39].

Monoclonal antibodies can be obtained, for example, from an animal cell immunized against CXCL13, or one of its fragments containing the epitope recognized by said monoclonal antibodies. Suitable fragments and peptides or polypeptides comprising them are described herein, and may be used to immunise animals to generate antibodies against CXCL13. Said CXCL13, or one of its fragments, can especially be produced according to the usual working methods, by genetic recombination starting with a nucleic acid sequence contained in the cDNA sequence coding for CXCL13 or fragment thereof, by peptide synthesis starting from a sequence of amino acids comprised in the peptide sequence of the CXCL13 and/or fragment thereof.

The monoclonal antibodies can, for example, be purified on an affinity column on which CXCL13 or one of its fragments containing the epitope recognized by said monoclonal antibodies, has previously been immobilized. More particularly, the monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. In one embodiment, the whole of these techniques can be used simultaneously or successively.

Antigen-binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region (VL) and an antibody heavy chain variable region (VH).

Isolated

This refers to the state in which binding members of the invention, or nucleic acid encoding such binding members, will generally be in accordance with the present invention. Thus, binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Isolated members and isolated nucleic acid will be free or substantially free of material with which they are naturally associated, such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

Heterogeneous preparations comprising anti-CXCL13 antibody molecules also form part of the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

As used herein, the phrase "substantially as set out" refers to the characteristic(s) of the relevant CDRs of the VH or VL domain of binding members described herein will be either identical or highly similar to the specified regions of which the sequence is set out herein. As described herein, the phrase "highly similar" with respect to specified region(s) of one or more variable domains, it is contemplated that from 1 to about 5, e.g. from 1 to 4, including 1 to 3, or 1 or 2, or 3 or 4, amino acid substitutions may be made in the CDR and/or VH or VL domain.

DETAILED DESCRIPTION OF THE INVENTION

As noted above, a binding member in accordance with the present invention binds CXCL13 and may neutralise a biological activity of CXCL13. A binding member of the present invention may be subjected to potency optimisation, to further improve its neutralizing potency. Generally, potency optimisation involves mutating the sequence of a selected binding member (normally the variable domain sequence of an antibody) to generate a library of binding members, which are then assayed for potency and the more potent binding members are selected. Thus selected "potency-optimised" binding members tend to have a higher potency than the binding member from which the library was generated.

Nevertheless, high potency binding members may be obtained without optimisation. As demonstrated herein, high potency binding members may be obtained directly from an initial screen e.g. a biochemical neutralization assay.

A "potency optimized" binding member refers to a binding member with an optimized potency of neutralization of a particular activity or downstream function of CXCL13. Assays and potencies are described in more detail elsewhere herein.

Potency-optimized and non-optimized binding members are aspects of the invention, as well as methods for potency optimization from a selected binding member. The present invention thus allows the skilled person to generate binding members having high potency.

In a further aspect, the present invention provides a method of obtaining one or more binding members able to bind the antigen, the method including bringing into contact a library of binding members according to the invention and said antigen, and selecting one or more binding members of the library able to bind said antigen.

The library may be displayed on particles or molecular complexes, e.g. replicable genetic packages, such as yeast, bacterial or bacteriophage (e.g. T7) particles, viruses, cells or covalent, ribosomal or other in vitro display systems, each particle or molecular complex containing nucleic acid encoding the antibody VH variable domain displayed on it, and optionally also a displayed VL domain if present. Phage display is described in WO92/01047 and e.g. U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160 and 6,521,404, each of which is herein incorporated by reference in their entirety.

Following selection of binding members able to bind the antigen and displayed on bacteriophage or other library particles or molecular complexes, nucleic acid may be taken from a bacteriophage or other particle or molecular complex displaying a said selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH variable domain with the amino acid sequence of an antibody VH variable domain of a said selected binding member may be provided in isolated form, as may a binding member comprising such a VH domain.

Ability to bind CXCL13 may be further tested, also ability to compete with a binding member e.g. an antibody 1, (e.g. in scFv format and/or IgG format, e.g. IgG1) for binding to CXCL13 may be determined. Ability to neutralize CXCL13 may be tested, as discussed further elsewhere herein.

A binding member according to the present invention may bind CXCL13 with the affinity of antibody 1, e.g. scFv or IgG1, or with an affinity that is better.

A binding member according to the present invention may neutralise a biological activity of CXCL13 with the potency of antibody 1, e.g. scFv, or IgG1, or with a potency that is better.

Binding affinity and neutralization potency of different binding members can be compared under appropriate conditions.

Variants of the VH and VL domains and CDRs of the present invention, including those for which amino acid sequences are set out herein, and which can be employed in binding members for CXCL13 can be obtained by means of methods of sequence alteration or mutation and screening for antigen-binding members with desired characteristics. Examples of desired characteristics include but are not limited to:

Increased binding affinity for antigen relative to known antibodies which are specific for the antigen Increased neutralization of an antigen activity relative to known antibodies which are specific for the antigen if the activity is known Specified competitive ability with a known antibody or ligand to the antigen at a specific molar ratio Ability to immunoprecipitate complex Ability to bind to a specified epitope
  Linear epitope, e.g. peptide sequence identified using peptide-binding scan as described herein, e.g. using peptides screened in linear and/or constrained conformation
  Conformational epitope, formed by non-continuous residues Ability to modulate a new biological activity of CXCL13, or downstream molecule.

Such methods are also provided herein.

Variants of antibody molecules disclosed herein may be produced and used in the present invention. Following the lead of computational chemistry in applying multivariate data analysis techniques to the structure/property-activity relationships [40] quantitative activity-property relationships of antibodies can be derived using well-known mathematical techniques, such as statistical regression, pattern recognition and classification [41, 42, 43, 44, 45, 46]. The properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites [47,48]. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions [47, 48].

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule [49] using any freely available or commercial package, such as WAM [50]. A protein visualisation and analysis software package, such as Insight II (Accelrys, Inc.) or Deep View [51] may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and binding members generally are available in the art. Variant sequences may be made, with substitutions that may or may not be predicted to have a minimal or beneficial effect on activity, and tested for ability to bind and/or neutralize CXCL13 and/or for any other desired property.

Variable domain amino acid sequence variants of any of the VH and VL domains whose sequences are specifically disclosed herein may be employed in accordance with the present invention, as discussed.

A further aspect of the invention is an antibody molecule comprising a VH domain that has at least 60, 70, 80, 85, 90, 95, 98 or 99% amino acid sequence identity with a VH domain of antibody 1 shown in the appended sequence listing, and/or comprising a VL domain that has at least 60, 70, 80, 85, 90, 95, 98 or 99% amino acid sequence identity with a VL domain of antibody 1 shown in the appended sequence listing. Algorithms that can be used to calculate % identity of two amino acid sequences include e.g. BLAST [52], FASTA [53], or the Smith-Waterman algorithm [54], e.g. employing default parameters.

Particular variants of VH domains, VL domains and/or CDRs or sets of CDRs may include one or more amino acid sequence alterations (addition, deletion, substitution and/or insertion of an amino acid residue). Variants may include less than about 20 alterations, such as less than about 15, less than about 10 or less than about 5 alterations, e.g. 5, 4, 3, 2 or 1.

Alterations may be made in one or more framework regions and/or one or more CDRs. The alterations normally do not result in loss of function, so a binding member comprising a thus-altered amino acid sequence may retain an ability to bind and/or neutralize CXCL13. It may retain the same quantitative binding and/or neutralizing ability as a binding member in which the alteration is not made, e.g. as measured in an assay described herein. The binding member comprising a thus-altered amino acid sequence may have an improved ability to bind and/or neutralize CXCL13.

Alteration may comprise replacing one or more amino acid residue with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine, etc. [55]. Those amino acid residues that are derivatised at their N-alpha position will only be located at the N-terminus of an amino-acid sequence. Normally in the present invention an amino acid is an L-amino acid, but it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention may comprise non-natural or non-standard amino acids described above. Non-standard amino acids (e.g. D-amino acids) may be incorporated into an amino acid sequence during synthesis, or by modification or replacement of the "original" standard amino acids after synthesis of the amino acid sequence.

Use of non-standard and/or non-naturally occurring amino acids increases structural and functional diversity, and can thus increase the potential for achieving desired CXCL13-binding and neutralizing properties in a binding member of the invention. Additionally, D-amino acids and analogues have been shown to have different pharmacokinetic profiles compared with standard L-amino acids, owing to in vivo degradation of polypeptides having L-amino acids after administration to an animal e.g. a human, meaning that D-amino acids are advantageous for some in vivo applications.

Novel VH or VL regions carrying CDR-derived sequences of the invention may be generated using random mutagenesis of one or more selected VH and/or VL genes to generate mutations within the entire variable domain. Such a technique is described by Gram et al. [56], who used error-prone PCR. In some embodiments one or two amino acid substitutions are made within an entire variable domain or set of CDRs.

Another method that may be used is to direct mutagenesis to CDR regions of VH or VL genes. Such techniques are disclosed by Barbas et al. [57] and Schier et al. [58].

All the above-described techniques are known as such in the art and the skilled person will be able to use such techniques to provide binding members of the invention using routine methodology in the art.

A further aspect of the invention provides a method for obtaining an antibody antigen-binding site for CXCL13, the method comprising providing by way of addition, deletion, substitution or insertion of one or more amino acids in the amino acid sequence of a VH domain set out herein, a VH domain which is an amino acid sequence variant of the VH domain, optionally combining the VH domain thus provided with one or more VL domains, and testing the VH domain or VH/VL combination or combinations to identify a binding member or an antibody antigen-binding site for CXCL13 and optionally with one or more desired properties, e.g. ability to neutralize CXCL13 activity. Said VL domain may have an amino acid sequence which is substantially as set out herein. An analogous method may be employed in which one or more sequence variants of a VL domain disclosed herein are combined with one or more VH domains.

As noted above, a CDR amino acid sequence substantially as set out herein may be carried as a CDR in a human antibody variable domain or a substantial portion thereof. The HCDR3 sequences substantially as set out herein represent embodiments of the present invention and each of these may be carried as a HCDR3 in a human heavy chain variable domain or a substantial portion thereof.

Variable domains employed in the invention may be obtained or derived from any germline or rearranged human variable domain, or may be a synthetic variable domain based on consensus or actual sequences of known human variable domains. A variable domain can be derived from a non-human antibody. A CDR sequence of the invention (e.g. CDR3) may be introduced into a repertoire of variable domains lacking a CDR (e.g. CDR3), using recombinant DNA technology. For example, Marks et al. [59] describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide binding members of the invention. The repertoire may then be displayed in a suitable host system, such as the phage display system of WO92/01047, which is herein incorporated by reference in its entirety, or any of a subsequent large body of literature, including Kay, Winter & McCafferty [60], so that suitable binding members may be selected. A repertoire may consist of from anything from $10^4$ individual members upwards, for example at least $10^5$, at least $10^6$, at least $10^7$, at least $10^8$, at least $10^9$ or at least $10^{10}$ members or more. Other suitable host systems include, but are not limited to yeast display, bacterial display, T7 display, viral display, cell display, ribosome display and covalent display.

A method of preparing a binding member for CXCL13 antigen is provided, which method comprises:

(a) providing a starting repertoire of nucleic acids encoding a VH domain which either include a CDR3 to be replaced or lack a CDR3 encoding region;

(b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;

(c) expressing the nucleic acids of said product repertoire;

(d) selecting a binding member for CXCL13; and (e) recovering said binding member or nucleic acid encoding it.

Again, an analogous method may be employed in which a VL CDR3 of the invention is combined with a repertoire of nucleic acids encoding a VL domain that either include a CDR3 to be replaced or lack a CDR3 encoding region.

Similarly, one or more, or all three CDRs may be grafted into a repertoire of VH or VL domains that are then screened for a binding member or binding members for CXCL13.

For example, one or more of the antibody 1 HCDR1, HCDR2 and HCDR3 or the antibody 1 set of HCDRs may be employed, and/or one or more of the antibody 1 LCDR1, LCDR2 and LCDR3 or the antibody 1 set of LCDRs may be employed.

Similarly, other VH and VL domains, sets of CDRs and sets of HCDRs and/or sets of LCDRs disclosed herein may be employed.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including antibody constant regions, other variable domains (for example in the production of diabodies) or detectable/functional labels as discussed in more detail elsewhere herein.

Although in some aspects of the invention, binding members comprise a pair of VH and VL domains, single binding domains based on either VH or VL domain sequences form further aspects of the invention. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain binding member able to bind CXCL13. This may be achieved by phage display screening methods using the so-called hierarchical dual combinatorial approach as disclosed in WO92/01047, herein incorporated by reference in its entirety, in which an individual colony containing either an H or L chain clone is used to infect a complete library of clones encoding the other chain (L or H) and the resulting two-chain binding member is selected in accordance with phage display techniques, such as those described in that reference. This technique is also disclosed in Marks et al, ibid.

Binding members of the present invention may further comprise antibody constant regions or parts thereof, e.g. human antibody constant regions or parts thereof. For example, a VL domain may be attached at its C-terminal end to antibody light chain constant domains including human Cκ or Cλ chains. Similarly, a binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG4. IgG1 is advantageous, due to its effector function and ease of manufacture. Any synthetic or other constant region variant that has these properties and stabilizes variable regions may also be useful in the present invention.

Binding members of the invention may be labelled with a detectable or functional label. Thus, a binding member or antibody molecule can be present in the form of an immunoconjugate so as to obtain a detectable and/or quantifiable signal. An immunoconjugate may comprise an antibody molecule of the invention conjugated with detectable or functional label. A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance.

Suitable labels include, by way of illustration and not limitation, enzymes, such as alkaline phosphatase, glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase e.g. horseradish peroxidase;

dyes;

fluorescent labels or fluorescers, such as fluorescein and its derivatives, fluorochrome, rhodamine compounds and derivatives, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cis Bio-international), chemoluminescent labels or chemiluminescers, such as isoluminol, luminol and the dioxetanes;

bio-luminescent labels, such as luciferase and luciferin;

sensitizers;

coenzymes;

enzyme substrates;

radiolabels including but not limited to bromine77, carbon14, cobalt57, fluorine8, gallium67, gallium 68, hydrogen3 (tritium), indium111, indium 113m, iodine123m, iodine125, iodine126, iodine131, iodine133, mercury107, mercury203, phosphorous32, rhenium99m, rhenium101, rhenium105, ruthenium95, ruthenium97, ruthenium103, ruthenium105, scandium47, selenium75, sulphur35, technetium99, technetium99m, tellurium121m, tellurium122m, tellurium125m, thulium165, thulium167, thulium168, yttrium199 and other radiolabels mentioned herein;

particles, such as latex or carbon particles; metal sol; crystallite; liposomes; cells, etc., which may be further labelled with a dye, catalyst or other detectable group;

molecules such as biotin, digoxygenin or 5-bromodeoxyuridine;

toxin moieties, such as for example a toxin moiety selected from a group of Pseudomonas exotoxin (PE or a cytotoxic fragment or mutant thereof), Diptheria toxin or a cytotoxic fragment or mutant thereof, a *botulinum* toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

Suitable enzymes and coenzymes are disclosed in Litman, et al., U.S. Pat. No. 4,275,149, and Boguslaski, et al., U.S. Pat. No. 4,318,980, each of which are herein incorporated by reference in their entireties. Suitable fluorescers and chemiluminescers are disclosed in Litman, et al., U.S. Pat. No. 4,275,149, which is incorporated herein by reference in its entirety. Labels further include chemical moieties, such as biotin that may be detected via binding to a specific cognate detectable moiety, e.g. labelled avidin or streptavidin. Detectable labels may be attached to antibodies of the invention using conventional chemistry known in the art.

Immunoconjugates or their functional fragments can be prepared by methods known to the person skilled in the art. They can be coupled to enzymes or to fluorescent labels directly or by the intermediary of a spacer group or of a linking group, such as a polyaldehyde, like glutaraldehyde, ethylenediaminetetraacetic acid (EDTA), diethylene-triaminepentaacetic acid (DPTA), or in the presence of coupling agents, such as those mentioned above for the therapeutic conjugates. Conjugates containing labels of fluorescein type can be prepared by reaction with an isothiocyanate.

The methods known to the person skilled in the art existing for coupling the therapeutic radioisotopes to the antibodies either directly or via a chelating agent, such as EDTA, DTPA mentioned above can be used for the radioelements which can be used in diagnosis. It is likewise possible to perform labelling with sodium125 by the chloramine T method [61] or else with technetium99m by the technique of Crockford et al., (U.S. Pat. No. 4,424,200, herein incorporated by reference in its entirety) or attached via DTPA as described by Hnatowich (U.S. Pat. No. 4,479,930, herein incorporated by reference in its entirety).

There are numerous methods by which the label can produce a signal detectable by external means, for example, by visual examination, electromagnetic radiation, heat, and chemical reagents. The label can also be bound to another binding member that binds the antibody of the invention, or to a support.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. This second wavelength emission may also transfer energy to a labelled acceptor molecule, and the resultant energy dissipated from the acceptor molecule by emission of light for example fluorescence resonance energy transfer (FRET). Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al. U.S. Pat. No. 5,185,243, which is herein incorporated herein by reference in its entirety.

The present invention provides a method comprising causing or allowing binding of a binding member as provided herein to CXCL13. As noted, such binding may take place in vivo, e.g. following administration of a binding member, or nucleic acid encoding a binding member, or it may take place in vitro, for example in ELISA, Western blotting, immunocytochemistry, immunoprecipitation, affinity chromatography, and biochemical or cell-based assays, such as a cAMP, calcium release or B cell chemotaxis assay.

The present invention also provides for measuring levels of antigen directly, by employing a binding member according to the invention for example in a biosensor system. For instance, the present invention comprises a method of detecting and/or measuring binding to CXCL13, comprising, (i) exposing said binding member to CXCL13 and (ii) detecting binding of said binding member to CXCL13, wherein binding is detected using any method or detectable label described herein. This, and any other binding detection method described herein, may be interpreted directly by the person performing the method, for instance, by visually observing a detectable label. Alternatively, this method, or any other binding detection method described herein, may produce a report in the form of an autoradiograph, a photograph, a computer printout, a flow cytometry report, a graph, a chart, a test tube or container or well containing the result, or any other visual or physical representation of a result of the method.

The amount of binding of binding member to CXCL13 may be determined. Quantitation may be related to the amount of the antigen in a test sample, which may be of diagnostic interest. Screening for CXCL13 binding and/or the quantitation thereof may be useful, for instance, in screening patients for diseases or disorders referred to herein and/or any other disease or disorder involving aberrant CXCL13 expression and/or activity.

A number of diseases are associated with increased levels of CXCL13. CXCL13 levels are a useful diagnostic and/or prognostic indicator for various disorders, for example, inflammatory and/or autoimmune diseases, as described elsewhere herein. For example, elevated levels of CXCL13 in e.g. serum or synovial fluid samples, may be used as a predictor of rheumatoid arthritis.

A diagnostic method of the invention may comprise (i) obtaining a tissue or fluid sample from a subject, (ii) exposing said tissue or fluid sample to one or more binding members of the present invention; and (iii) detecting bound CXCL13 as compared with a control sample, wherein an increase in the amount of CXCL13 binding as compared with the control may indicate an aberrant level of CXCL13 expression or activity. Tissue or fluid samples to be tested include blood, serum, urine, biopsy material, tumours, or any tissue suspected of containing aberrant CXCL13 levels. Subjects testing positive for aberrant CXCL13 levels or activity may also benefit from the treatment methods disclosed later herein.

Those skilled in the art are able to choose a suitable mode of determining binding of the binding member to an antigen according to their preference and general knowledge, in light of the methods disclosed herein.

The reactivities of binding members in a sample may be determined by any appropriate means. Radioimmunoassay (RIA) is one possibility. Radioactive labelled antigen is mixed with unlabelled antigen (the test sample) and allowed to bind to the binding member. Bound antigen is physically separated from unbound antigen and the amount of radioactive antigen bound to the binding member determined. The more antigen there is in the test sample the less radioactive antigen will bind to the binding member. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red, and lanthanide chelates or cryptates. Suitable chromogenic dyes include diaminobenzidine.

Other reporters include macromolecular colloidal particles or particulate material, such as latex beads that are colored, magnetic or paramagnetic, and biologically or chemically active agents that can directly or indirectly cause detectable signals to be visually observed, electronically detected or otherwise recorded. These molecules may be enzymes, which catalyze reactions that develop, or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual binding member-reporter conjugates may be used to derive quantifiable absolute or relative data of the relevant binding member binding in samples (normal and test).

A kit comprising a binding member according to any aspect or embodiment of the present invention is also provided as an aspect of the present invention. In the kit, the binding member may be labelled to allow its reactivity in a sample to be determined, e.g. as described further below. Further the binding member may or may not be attached to a solid support. Components of a kit are generally sterile and in sealed vials or other containers. Kits may be employed in diagnostic analysis or other methods for which binding members are useful. A kit may contain instructions for use of the components in a method, e.g. a method in accordance with the present invention. Ancillary materials to assist in or to enable performing such a method may be included within a kit of the invention. The ancillary materials include a second, different binding member which binds to the first binding member and is conjugated to a detectable label (e.g., a fluorescent label, radioactive isotope or enzyme). Antibody-based kits may also comprise beads for conducting an immunoprecipitation. Each component of the kits is generally in its own suitable container. Thus, these kits generally comprise distinct containers suitable for each binding member. Further, the kits may comprise instructions for performing the assay and methods for interpreting and analyzing the data resulting from the performance of the assay.

The present invention also provides the use of a binding member as above for measuring antigen levels in a competition assay, that is to say a method of measuring the level of antigen in a sample by employing a binding member as provided by the present invention in a competition assay. This may be where the physical separation of bound from unbound antigen is not required. Linking a reporter molecule to the binding member so that a physical or optical change occurs on binding is one possibility. The reporter molecule may directly or indirectly generate detectable signals, which may be quantifiable. The linkage of reporter molecules may be directly or indirectly, covalently, e.g. via a peptide bond or non-covalently. Linkage via a peptide bond may be as a result of recombinant expression of a gene fusion encoding antibody and reporter molecule.

In various aspects and embodiments, the present invention extends to a binding member that competes for binding to CXCL13, e.g. human CXCL13, with any binding member defined herein, e.g. antibody 1, e.g. in IgG1 format. Competition between binding members may be assayed easily in vitro, for example by tagging a specific reporter molecule to one binding member which can be detected in the presence of other untagged binding member(s), to enable identification of binding members which bind the same epitope or an overlapping epitope. Competition may be determined for example using ELISA in which CXCL13 is immobilized to a plate and a first tagged or labelled binding member along with one or more other untagged or unlabelled binding members is added to the plate. Presence of an untagged binding member that competes with the tagged binding member is observed by a decrease in the signal emitted by the tagged binding member. In one example, a HTRF® epitope competition assay may be used.

For example, the present invention includes a method of identifying a CXCL13 binding compound, comprising (i) immobilizing CXCL13 to a support, (ii) contacting said immobilized CXCL13 simultaneously or in a step-wise manner with at least one tagged or labelled binding member according to the invention and one or more untagged or unlabelled test binding compounds, and (iii) identifying a new CXCL13 binding compound by observing a decrease in the amount of bound tag from the tagged binding member. Such methods can be performed in a high-throughput manner using a multiwell or array format. Such assays may be also be performed in solution. See, for instance, U.S. Pat. No. 5,814,468, which is herein incorporated by reference in its entirety. As described above, detection of binding may be interpreted directly by the person performing the method, for instance, by visually observing a detectable label, or a decrease in the presence thereof. Alternatively, the binding methods of the invention may produce a report in the form of an autoradiograph, a photograph, a computer printout, a flow cytometry report, a graph, a chart, a test tube or container or well containing the result, or any other visual or physical representation of a result of the method.

Competition assays can also be used in epitope mapping. In one instance epitope mapping may be used to identify the epitope bound by a CXCL13 binding member which optionally may have optimized neutralizing and/or modulating characteristics. Such an epitope can be linear or conformational. A conformational epitope can comprise at least two different fragments of CXCL13, wherein said fragments are positioned in proximity to each other when CXCL13 is folded in its tertiary or quaternary structure to form a conformational epitope which is recognized by an inhibitor of CXCL13, such as a CXCL13-binding member. In testing for competition a peptide fragment of the antigen may be employed, especially a peptide including or consisting essentially of an epitope of interest. A peptide having the epitope sequence plus one or more amino acids at either end may be used. Binding members according to the present invention may be such that their binding for antigen is inhibited by a peptide with or including the sequence given.

The present invention further provides an isolated nucleic acid encoding a binding member of the present invention. Nucleic acid may include DNA and/or RNA. In one aspect, the present invention provides a nucleic acid that codes for a CDR or set of CDRs or VH domain or VL domain or antibody antigen-binding site or antibody molecule, e.g. scFv or IgG1, of the invention as defined above.

The present invention also provides constructs in the form of plasmids, vectors, transcription or expression cassettes which comprise at least one polynucleotide as above.

The present invention also provides a recombinant host cell that comprises one or more constructs as above. A nucleic acid encoding any CDR or set of CDRs or VH domain or VL domain or antibody antigen-binding site or antibody molecule, e.g. scFv or IgG1, as provided, itself forms an aspect of the present invention, as does a method of production of the encoded product, which method comprises expression from encoding nucleic acid therefore. Expression may conveniently be achieved by culturing under appropriate conditions recombinant host cells containing the nucleic acid. Following production by expression a VH or VL domain, or binding member may be isolated and/or purified using any suitable technique, then used as appropriate.

Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and binding members comprising a VH and/or VL domain are provided as further aspects of the present invention.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals. The expression of antibodies and antibody fragments in prokaryotic cells is well established in the art. For a review, see for example Plückthun [62]. A common bacterial host is E. coli.

Expression in eukaryotic cells in culture is also available to those skilled in the art as an option for production of a binding member [63, 64, 65]. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate [66]. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. [67].

A further aspect of the present invention provides a host cell containing nucleic acid as disclosed herein. Such a host cell may be in vitro and may be in culture. Such a host cell may be in vivo. In vivo presence of the host cell may allow intra-cellular expression of the binding members of the present invention as "intrabodies" or intra-cellular antibodies. Intrabodies may be used for gene therapy.

A still further aspect provides a method comprising introducing nucleic acid of the invention into a host cell. The introduction may employ any available technique. For eukaryotic cells, suitable techniques may include calcium phosphate transfection, DEAF-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene. The purification of the expressed product may be achieved by methods known to one of skill in the art.

Nucleic acid of the invention may be integrated into the genome (e.g. chromosome) of the host cell. Integration may be promoted by inclusion of sequences that promote recombination with the genome, in accordance with standard techniques.

The present invention also provides a method that comprises using a construct as stated above in an expression system in order to express a binding member or polypeptide as above.

Binding members of the present invention may be used in methods of diagnosis or treatment in human or animal subjects, e.g. humans. Binding members for CXCL13 may be used to treat disorders associated with CXCL13, e.g. associated with aberrant CXCL13 expression and/or activity. There is evidence for involvement of CXCL13 in a variety of disorders, as discussed elsewhere herein. Binding members of the invention may be used to inhibit binding of CXCL13 to CXCR5 and thereby to treat a disease or disorder mediated by CXCL13 binding to CXCR5. Disorders associated with CXCL13 include disorders that are caused and/or exacerbated by CXCL13 binding to its receptor CXCR5. Aspects of the invention relate to treatment of such disorders by alleviating or ameliorating one or more symptoms and/or causes of the disorder.

Binding members for CXCL13 may be used to inhibit or reduce aberrant formation and/or development of lymphoid follicles, e.g. ectopic lymphoid follicles, such as those found in arthritic synovium. Binding members may inhibit or reduce: CXCL13-CXCR5 signalling mediated recruitment of B cells and/or dendritic cells and/or follicular B helper T cells, to follicles; and/or reduce immunoglobulin production by follicular B cells; and/or inhibit or reduce follicular B cell production of cytokines and/or activation of T cells. Binding members may also be used to inhibit or reduce aberrant bone and/or cartilage destruction.

Binding members may thus be used for the treatment of diseases or disorders associated with aberrant or ectopic lymphoid follicles. Disorders associated with ectopic lymphoid follicles include rheumatoid arthritis, Sjogrens syndrome, multiple sclerosis, myasthenia gravis, systemic lupus erythmatosis (SLE), autoimmune thyroid diseases (e.g. Grave's disease, Hashimoto's thyroiditis), chronic infection e.g. Lyme Neuroborreliosis and acute cardiac rejection featuring Quilty effect.

For example inflamed arthritic synovium is generally characterised by: ectopic lymphoid follicles containing germinal centres; inflammatory cell infiltrate; B cell production of auto-antibodies and cytokines; B cell activation of T cells; and/or bone and cartilage destruction. Binding members may disrupt formation of the ectopic follicles as described herein and thus inhibit B cell autoantibody production and/or synovial inflammation. Thus binding members may be used in the treatment of arthritic disorders such as rheumatoid arthritis (RA), and/or osteoarthritis.

Binding members of the invention may be used for treatment of bone and/or joint diseases or disorders, especially diseases or disorders associated with destruction and/or remodelling of bone and/or cartilage, e.g. aberrant turnover of bone or cartilage. For example, binding members may be used to treat rheumatoid arthritis and/or osteoarthritis.

Binding members of the invention may be used to inhibit lymphocyte (e.g. B and/or T cell) chemotaxis, and may thus be used to treat disorders associated with lymphocyte chemotaxis such as viral infection (e.g. HIV infection) and leukaemia (e.g. T-cell lineage acute lymphocytic leukaemia and B-cell lineage acute and chronic lymphocytic leukaemia).

Binding members of the invention may be used to inhibit proliferation of lymphomas and may thus be used to treat disorders associated with lymphoma proliferation, such as leukaemia (e.g. T-cell lineage acute lymphocytic leukaemia and B-cell lineage acute and chronic lymphocytic leukaemia).

Binding members for CXCL13 may be used to inhibit aberrant formation and/or development of lymphoid follicles, e.g. ectopic lymphoid follicles, inhibit aberrant bone and/or cartilage destruction and/or remodelling, and/or to inhibit chemotaxis of lymphocytes and/or proliferation of lymphomas as described herein. Accordingly, the invention provides a method of inhibiting aberrant formation and/or development of lymphoid follicles, e.g. ectopic lymphoid follicles, inhibiting aberrant bone and/or cartilage destruction and/or remodelling, and/or inhibiting chemotaxis of lymphocytes and/or proliferation of lymphomas, comprising administering to a patient in need thereof an effective amount of one or more binding members of the present invention alone or in a combined therapeutic regimen with another appropriate medicament known in the art or described herein such that the aberrant formation and/or development of lymphoid follicles, e.g. ectopic lymphoid follicles, aberrant bone and/or cartilage destruction and/or remodelling, and/or chemotaxis of lymphocytes and/or proliferation of lymphomas is or are inhibited.

Binding members of the invention may be used in the diagnosis of diseases or disorders associated with CXCL13 e.g. in which levels of CXCL13 are altered e.g. elevated relevant to normal levels. Binding members may be used in diagnosis of one or more diseases or disorders described herein, including for example rheumatoid arthritis, Sjogren's syndrome, HIV, myasthenia gravis, angioimmunoblastic T-cell lymphoma and transmissible spongiform encephalopathy (TSE).

Evidence for involvement of CXCL13 in certain disorders is described below and elsewhere herein. In addition, the data presented herein further indicates that binding members of the invention can be used to treat such disorders, including preventative treatment and reduction of severity of the disorders. Accordingly, the invention provides a method of treating or reducing the severity of at least one symptom of any of the disorders mentioned herein, comprising administering to a patient in need thereof an effective amount of one or more binding members of the present invention alone or in a combined therapeutic regimen with another appropriate medicament known in the art or described herein such that the severity of at least one symptom of any of the above disorders is reduced.

Evidence for the role of CXCL13 in the development of peripheral lymphoid organs and in innate immunity is described in part elsewhere herein.

In addition to this, several lines of evidence indicate a role for CXCL13 in the pathogenesis of rheumatoid arthritis (RA) in man. For example, expression of CXCL13 mRNA and protein is elevated in RA synovium [68], there is a positive correlation between the levels of CXCL13 protein in RA synovium and disease severity [69]. We have also discovered that elevated levels of CXCL13 have been measured in the serum and synovial fluid of RA patients, indicating that binding members of the invention may be used in methods of diagnosing RA as described herein.

Inflamed synovium is characterised by an inflammatory cell infiltrate and the presence of organised lymphocyte aggregates that resemble lymphoid tissue. These ectopic lymphoid structures contain features of germinal centres including the presence of FDCs, and high endothelial venules (HEVs). Germinal centres provide a microenvironment that supports B cell differentiation into plasma cells and the generation of high affinity antibodies such as rheumatoid factor [70]. CXCL13 protein in RA synovium has been immunolocalised to FDCs within germinal centres [69] and macrophages in the cellular infiltrate [71]. In RA lesions, CXCL13 is strongly predictive of ectopic lymphoid follicle formation and the development of germinal centre reactions (Takemura, S. et al. J. Immunol. 167: 1072-1080, 2001).

The role of CXCL13 in RA is further supported by in vivo evidence from animal models of disease. Prophylactic dosing of a CXCL13 neutralising antibody reduces disease severity in collagen induced arthritis (CIA) in the mouse, with a concomitant reduction in inflammatory cell infiltration into the arthritic joint and a reduction in the degree of cartilage and bone erosion [72]. In the CIA model, follicles in both the spleen and joints of mice treated with an anti-CXCL13 antibody contain fewer germinal centres and the germinal centres are smaller in size compared with control mice [72].

Other studies have shown that mice deficient in CXCR5 develop less severe symptoms in an adjuvant-induced arthritis (AIA) model with a reduction in synovial inflammation and joint destruction (Hartmann, S. et al, European Congress on Immunology, abstract 2672, 2006). The formation of organised germinal centres, the levels of anti-antigen antibodies and antigen-induced T cell proliferative responses were also reduced in this study.

A role for CXCL13 in bone and cartilage turnover has also been demonstrated by in vitro evidence from cultured chondrocytes and osteoblasts. CXCR5 is expressed on chondrocytes isolated from articular cartilage from osteoarthritis (OA) patients. Treatment of these chondrocytes in culture conditions with CXCL13 induces the release of matrix metalloproteinases (MMPs) and cathepsin B as well as inducing proliferation [73]. CXCL13 also induces the proliferation of cultured osteoblasts derived from OA patients and the expression of interleukin-1 (IL-1) mRNA [74]. Basal secretion of CXCL13 from cultured osteoblasts can also be enhanced by treatment with IL-1 [75]. In bone samples taken from RA patients undergoing joint surgery, CXCL13 protein is immunolocalised to mononuclear cell aggregates in bone marrow containing features of lymphoid neogenesis [76].

The CXCR5 receptor is expressed on a subset of memory T cells with B cell helper function, which are designated follicular B helper T cells ($T_{FH}$). CXCL13 induces the chemotaxis of CXCR5-expressing $T_{FH}$ cells isolated from human tonsil [77], while in secondary lymphoid organs, CXCR5-positive $T_{FH}$ cells localise to B cell follicles and germinal centres where they support immunoglobulin production [78]. $T_{FH}$ cells freshly isolated from germinal centres secrete low levels of CXCL13 but this is significantly elevated following stimulation through the TCR and CD28 (Kim, C H. et al. Blood, 104: 1952-1960, 2004).

A subset of dendritic cells has been identified that express CXCR5 and which localise to lymphoid follicles in response to CXCL13 [79]. This response is dependent on B cell-derived membrane bound lymphotoxin which stimulates the expression of CXCL13 by follicular stromal cells and establishes the chemotactic gradient necessary to recruit CXCR5-positive cells into the follicles.

Although inhibition of B cell trafficking is unprecedented in the clinic, there is clinical precedent for efficacy of B cell depletion therapy in RA patients [80]. B cell depletion with a chimeric anti-CD20 monoclonal antibody is effective and well tolerated with patients experiencing sustained periods of disease remission ranging from months to years following a single course of treatment. Reduction of autoantibody levels is a key mechanism of the success of B cell depletion as clinical relapse correlates with the return of serum autoantibodies to pre-treatment levels [81]. In addition to autoantibody production, B cells are thought to contribute to RA progression through cytokine production and activation of T cells through antigen presentation.

The inhibition of B cell trafficking by CXCL13 neutralisation represents a novel approach for the treatment of RA. CXCL13 neutralisation has the potential both to inhibit autoantibody production and synovial inflammation through disruption of ectopic follicles and germinal centre reactions in RA synovium. CXCL13 neutralisation may also provide additional benefit by preventing bone and cartilage destruction by direct and indirect mechanisms.

Elevated levels of CXCL13 have been described in HIV (Widney, D P. et al. J. Int. Cyt. Res. 25: 702-706, 2005). The use of CXCL13 as surrogate marker for transmissible spongiform encephalopathy (TSE) has also been reported (EP1703282A1).

A binding member of the invention may be used in the treatment of any of the following:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

Binding members of the invention may be used in animals or in animal models of disease, including mice, rats, rabbits, guinea pigs, monkeys, fish, dogs, cows, goats, horses, etc. Animal models involving the CXCL13/CXCR5 signalling system are known in the art. For example, animal models of rheumatoid arthritis are known, e.g. CIA, AIA and Streptococcal cell wall (SCW) models. An animal model of MS is the experimental autoimmune encephalomyelitis (EAE) mouse model. Mouse models of SLE include the MRL/lpr mouse model and the NZB×NZW $F_1$ ($BWF_1$) mouse model.

Thus, the binding members of the present invention are useful as therapeutic agents in the treatment of diseases or disorders involving CXCL13, e.g. CXCL13 expression and/or activity, especially aberrant expression/activity. A method of treatment may comprise administering an effective amount of a binding member of the invention to a patient in need thereof, wherein aberrant expression and/or activity of CXCL13 is decreased. A method of treatment may comprise (i) identifying a patient demonstrating aberrant CXCL13 levels or activity, for instance using the diagnostic methods described above, and (ii) administering an effective amount of a binding member of the invention to the patient, wherein aberrant expression and/or activity of CXCL13 is decreased. An effective amount according to the invention is an amount that decreases the aberrant expression and/or activity of CXCL13 so as to decrease or lessen the severity of at least one symptom of the particular disease or disorder being treated, but not necessarily cure the disease or disorder.

The invention also provides a method of antagonising at least one effect of CXCL13 comprising contacting with or administering an effective amount of one or more binding members of the present invention such that said at least one effect of CXCL13 is antagonised. Effects of CXCL13 that may be antagonised by the methods of the invention include binding to CXCR5, and any downstream effects that arise as a consequence of these binding reactions. Thus, the binding members of the present invention are useful as therapeutic agents in the treatment of diseases or disorders involving CXCL13-CXCR5 signalling, especially aberrant CXCL13-CXCR5 signalling.

Accordingly, further aspects of the invention provide methods of treatment comprising administration of a binding member as provided, pharmaceutical compositions comprising such a binding member, and use of such a binding member in the manufacture of a medicament for administration, for example in a method of making a medicament or pharmaceutical composition comprising formulating the binding member with a pharmaceutically acceptable excipient.

A pharmaceutically acceptable excipient may be a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Binding members of the present invention will usually be administered in the form of a pharmaceutical composition, which may comprise at least one component in addition to the binding member. Thus pharmaceutical compositions according to the present invention, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, inhaled, intra-tracheal, topical, intra-vesicular or by injection, as discussed below.

Pharmaceutical compositions for oral administration, such as for example single domain antibody molecules (e.g. "nanobodies™") etc are also envisaged in the present invention. Such oral formulations may be in tablet, capsule, powder, liquid or semi-solid form. A tablet may comprise a solid carrier, such as gelatin or an adjuvant. Liquid pharmaceutical compositions generally comprise a liquid carrier, such as water, petroleum, animal or vegetable oils, mineral oil or synthetic oil. Physiological saline solution, dextrose or other saccharide solution or glycols, such as ethylene glycol, propylene glycol or polyethylene glycol may be included.

For intra-venous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

Binding members of the present invention may be formulated in liquid, semi-solid or solid forms depending on the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by lyophilisation, spray drying, or drying by supercritical fluid technology, for example. Formulations of anti-CXCL13 will depend upon the intended route of delivery: for example, formulations for pulmonary delivery may consist of particles with physical properties that ensure penetration into the deep lung upon inhalation; topical formulations (e.g. for treatment of scarring, e.g. dermal scarring) may include viscosity modifying agents, which prolong the time that the drug is resident at the site of action. A binding member may be prepared with a carrier that will protect the binding member against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known to those skilled in the art [82].

Anti-CXCL13 treatment may be given orally (such as for example single domain antibody molecules (e.g. "nanobodies™")) by injection (for example, subcutaneously, intra-articular, intra-venously, intra-peritoneal, intra-arterial or intra-muscularly), by inhalation, intra-tracheal, by the intra-vesicular route (instillation into the urinary bladder), or topically (for example intra-ocular, intra-nasal, rectal, into wounds, on skin). The treatment may be administered by pulse infusion, particularly with declining doses of the binding member. The route of administration can be determined by the physicochemical characteristics of the treatment, by special considerations for the disease or by the requirement to optimize efficacy or to minimize side-effects. One particular route of administration is intra-venous. Another route of administering pharmaceutical compositions of the present invention is subcutaneously. It is envisaged that anti-CXCL13 treatment will not be restricted to use in the clinic. Therefore, subcutaneous injection using a needle-free device is also advantageous.

A composition may be administered alone or in combination with other treatments, either simultaneously or sequentially dependent upon the condition to be treated.

A binding member for CXCL13 may be used as part of a combination therapy in conjunction with an additional medicinal component. Combination treatments may be used to provide significant synergistic effects, particularly the combination of an anti-CXCL13 binding member with one or more other drugs. A binding member for CXCL13 may be administered concurrently or sequentially or as a combined preparation with another therapeutic agent or agents, for the treatment of one or more of the conditions listed herein.

A binding member according to the present invention may be provided in combination or addition with one or more of the following agents:

- a cytokine or agonist or antagonist of cytokine function (e.g. an agent which acts on cytokine signalling pathways, such as a modulator of the SOCS system), such as an alpha-, beta- and/or gamma-interferon; insulin-like growth factor type I (IGF-1), its receptors and associated binding proteins; interleukins (IL), e.g. one or more of IL-1 to -33, and/or an interleukin antagonist or inhibitor, such as anakinra; inhibitors of receptors of interleukin family members or inhibitors of specific subunits of such receptors, a tumour necrosis factor alpha (TNF-α) inhibitor, such as an anti-TNF monoclonal antibodies (for example infliximab, adalimumab and/or CDP-870) and/or a TNF receptor antagonist, e.g. an immunoglobulin molecule (such as etanercept) and/or a low-molecular-weight agent, such as pentoxyfylline;
- a modulator of B cells, e.g. a monoclonal antibody targeting B-lymphocytes (such as CD20 (rituximab, MRA-aIL16R or Belimumab) or T-lymphocytes (e.g. CTLA4-Ig (Abatacept), HuMax Il-15);
- a modulator of B cell activation, maturation or survival (such as Atacicept);
- a modulator of immune function, e.g. an antagonist of lymphotoxin LIGHT pathways (such as LTBR-Fc)
- a modulator that inhibits osteoclast activity, for example an antibody to RANKL;
- a modulator of chemokine or chemokine receptor function, such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 and CXCR6 (for the C—X—C family) and $CX_3CR1$ for the C—$X_3$—C family;
- an inhibitor of matrix metalloproteases (MMPs), i.e. one or more of the stromelysins, the collagenases and the gelatinases as well as aggrecanase, especially collagenase-1 (MMP-1), collagenase-2 (MMP-8), collagenase-3 (MMP-13), stromelysin-1 (MMP-3), stromelysin-2 (MMP-10) and/or stromelysin-3 (MMP-11) and/or MMP-9 and/or MMP-12, e.g. an agent such as doxycycline;
- a leukotriene biosynthesis inhibitor, 5-lipoxygenase (5-LO) inhibitor or 5-lipoxygenase activating protein (FLAP) antagonist, such as zileuton; ABT-761; fenleuton; tepoxalin; Abbott-79175; Abbott-85761; N-(5-substituted)-thiophene-2-alkylsulfonamides; 2,6-di-tert-butylphenolhydrazones; methoxytetrahydropyrans such as Zeneca ZD-2138; the compound SB-210661; a pyridinyl-substituted 2-cyanonaphthalene compound, such as L-739,010; a 2-cyanoquinoline compound, such as L-746,530; indole and/or a quinoline compound, such as MK-591, MK-886 and/or BAY×1005;
- a receptor antagonist for leukotrienes (LT) B4, LTC4, LTD4, and LTE4, selected from the group consisting of the phenothiazin-3-1s, such as L-651,392; amidino compounds, such as CGS-25019c; benzoxalamines, such as ontazolast; benzenecarboximidamides, such as BIIL 284/260; and compounds, such as zafirlukast, ablukast, montelukast, pranlukast, verlukast (MK-679), RG-12525, Ro-245913, iralukast (CGP 45715A) and BAY×7195;
- a phosphodiesterase (PDE) inhibitor, such as a methylxanthanine, e.g. theophylline and/or aminophylline; and/or a selective PDE isoenzyme inhibitor, e.g. a PDE4 inhibitor and/or inhibitor of the isoform PDE4D and/or an inhibitor of PDE5;
- a histamine type 1 receptor antagonist, such as cetirizine, loratadine, desloratadine, fexofenadine, acrivastine, terfenadine, astemizole, azelastine, levocabastine, chlorpheniramine, promethazine, cyclizine, and/or mizolastine (generally applied orally, topically or parenterally);
- a proton pump inhibitor (such as omeprazole) or gastroprotective histamine type 2 receptor antagonist;
- an antagonist of the histamine type 4 receptor;
- an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride and ethylnorepinephrine hydrochloride;
- an anticholinergic agent, e.g. a muscarinic receptor (M1, M2, and M3) antagonist, such as atropine, hyoscine, glycopyrrrolate, ipratropium bromide, tiotropium bromide, oxitropium bromide, pirenzepine and telenzepine;
- a beta-adrenoceptor agonist (including beta receptor subtypes 1-4), such as isoprenaline, salbutamol, formoterol, salmeterol, terbutaline, orciprenaline, bitolterol mesylate and/or pirbuterol, e.g. a chiral enantiomer thereof;
- a chromone, e.g. sodium cromoglycate and/or nedocromil sodium;
- a glucocorticoid, such as flunisolide, triamcinolone acetonide, beclomethasone dipropionate, budesonide, fluticasone propionate, ciclesonide, and/or mometasone furoate;
- an agent that modulate nuclear hormone receptors, such as a PPAR;
- an immunoglobulin (Ig) or Ig preparation or an antagonist or antibody modulating Ig function, such as anti-IgE (e.g. omalizumab);
- other systemic or topically-applied anti-inflammatory agent, e.g. thalidomide or a derivative thereof, a retinoid, dithranol and/or calcipotriol;

combinations of aminosalicylates and sulfapyridine, such as sulfasalazine, mesalazine, balsalazide, and olsalazine; and immunomodulatory agents, such as the thiopurines; and corticosteroids, such as budesonide;

an antibacterial agent, e.g. a penicillin derivative, a tetracycline, a macrolide, a beta-lactam, a fluoroquinolone, metronidazole and/or an inhaled aminoglycoside; and/or an antiviral agent, e.g. acyclovir, famciclovir, valaciclovir, ganciclovir, cidofovir; amantadine, rimantadine; ribavirin; zanamavir and/or oseltamavir; a protease inhibitor, such as indinavir, nelfinavir, ritonavir and/or saquinavir; a nucleoside reverse transcriptase inhibitor, such as didanosine, lamivudine, stavudine, zalcitabine, zidovudine; a non-nucleoside reverse transcriptase inhibitor, such as nevirapine, efavirenz;

a cardiovascular agent, such as a calcium channel blocker, beta-adrenoceptor blocker, angiotensin-converting enzyme (ACE) inhibitor, angiotensin-2 receptor antagonist; lipid lowering agent, such as a statin and/or fibrate; a modulator of blood cell morphology, such as pentoxyfylline; a thrombolytic and/or an anticoagulant, e.g. a platelet aggregation inhibitor;

a CNS agent, such as an antidepressant (such as sertraline), anti-Parkinsonian drug (such as deprenyl, L-dopa, ropinirole, pramipexole; MAOB inhibitor, such as selegine and rasagiline; comP inhibitor, such as tasmar; A-2 inhibitor, dopamine reuptake inhibitor, NMDA antagonist, nicotine agonist, dopamine agonist and/or inhibitor of neuronal nitric oxide synthase) and an anti-Alzheimer's drug, such as donepezil, rivastigmine, tacrine, COX-2 inhibitor, propentofylline or metrifonate;

an agent for the treatment of acute and chronic pain, e.g. a centrally or peripherally-acting analgesic, such as an opioid analogue or derivative, carbamazepine, phenytoin, sodium valproate, amitryptiline or other antidepressant agent, paracetamol, or non-steroidal anti-inflammatory agent;

a parenterally or topically-applied (including inhaled) local anaesthetic agent, such as lignocaine or an analogue thereof;

an anti-osteoporosis agent, e.g. a hormonal agent, such as raloxifene, or a biphosphonate, such as alendronate;

(i) a tryptase inhibitor; (ii) a platelet activating factor (PAF) antagonist; (iii) an interleukin converting enzyme (ICE) inhibitor; (iv) an IMPDH inhibitor; (v) an adhesion molecule inhibitors including VLA-4 antagonist; (vi) a cathepsin; (vii) a kinase inhibitor, e.g. an inhibitor of tyrosine kinases (such as Btk, Itk, Jak3 MAP examples of inhibitors might include Gefitinib, Imatinib mesylate), a serine/threonine kinase (e.g. an inhibitor of MAP kinase, such as p38, JNK, protein kinases A, B and C and IKK), or a kinase involved in cell cycle regulation (e.g. a cylin dependent kinase); (viii) a glucose-6 phosphate dehydrogenase inhibitor; (ix) a kinin-B$_1$- and/or B$_2$-receptor antagonist; (x) an anti-gout agent, e.g. colchicine; (xi) a xanthine oxidase inhibitor, e.g. allopurinol; (xii) a uricosuric agent, e.g. probenecid, sulfinpyrazone, and/or benzbromarone; (xiii) a growth hormone secretagogue; (xiv) transforming growth factor (TGFβ); (xv) platelet-derived growth factor (PDGF); (xvi) fibroblast growth factor, e.g. basic fibroblast growth factor (bFGF); (xvii) granulocyte macrophage colony stimulating factor (GM-CSF); (xviii) capsaicin cream; (xix) a tachykinin NK$_1$. and/or NK$_3$. receptor antagonist, such as NKP-608C, SB-233412 (talnetant) and/or D-4418; (xx) an elastase inhibitor, e.g. UT-77 and/or ZD-0892; (xxi) a TNF-alpha converting enzyme inhibitor (TACE); (xxii) induced nitric oxide synthase (iNOS) inhibitor or (xxiii) a chemoattractant receptor-homologous molecule expressed on TH2 cells (such as a CRTH2 antagonist); (xxiv) an inhibitor of a P38 (xxv) agent modulating the function of Toll-like receptors (TLR) and (xxvi) an agent modulating the activity of purinergic receptors, such as P2X7; (xxvii) an inhibitor of transcription factor activation, such as NFkB, API, and/or STATS.

An inhibitor may be specific or may be a mixed inhibitor, e.g. an inhibitor targeting more than one of the molecules (e.g. receptors) or molecular classes mentioned above.

The binding member could also be used in association with a chemotherapeutic agent or another tyrosine kinase inhibitor in co-administration or in the form of an immunoconjugate. Fragments of said antibody could also be use in bispecific antibodies obtained by recombinant mechanisms or biochemical coupling and then associating the specificity of the above described antibody with the specificity of other antibodies able to recognize other molecules involved in the activity for which CXCL13 is associated.

For treatment of an inflammatory disease, e.g. rheumatoid arthritis, osteoarthritis, asthma, allergic rhinitis, chronic obstructive pulmonary disease (COPD), or psoriasis, a binding member of the invention may be combined with one or more agents, such as non-steroidal anti-inflammatory agents (hereinafter NSAIDs) including non-selective cyclo-oxygenase (COX)-1/COX-2 inhibitors whether applied topically or systemically, such as piroxicam, diclofenac, propionic acids, such as naproxen, flurbiprofen, fenoprofen, ketoprofen and ibuprofen, fenamates, such as mefenamic acid, indomethacin, sulindac, azapropazone, pyrazolones, such as phenylbutazone, salicylates, such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intra-muscular, intra-venous or intra-articular routes); methotrexate, leflunomide; hydroxychloroquine, d-penicillamine, auranofin or other parenteral or oral gold preparations; analgesics; diacerein; intra-articular therapies, such as hyaluronic acid derivatives; and nutritional supplements, such as glucosamine.

A binding member of the invention can also be used in combination with an existing therapeutic agent for the treatment of cancer. Suitable agents to be used in combination include:

(i) antiproliferative/antineoplastic drugs and combinations thereof, as used in medical oncology, such as Gleevec (imatinib mesylate), alkylating agents (for example cisplatin, carboplatin, cyclophosphamide, nitrogen mustard, melphalan, chlorambucil, busulphan and nitrosoureas); antimetabolites (for example antifolates, such as fluoropyrimidines like 5-fluorouracil and tegafur, raltitrexed, methotrexate, cytosine arabinoside, hydroxyurea, gemcitabine and paclitaxel); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecins);

(ii) cytostatic agents, such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase, such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor (for example the anti-vascular endothelial cell growth factor antibody bevacizumab, compounds, such as those disclosed in International Patent Applications WO 97/22596, WO 97/30035, WO 97/32856 and WO 98/13354, each of which is incorporated herein in its entirety) and compounds that work by other mechanisms (for example linomide, inhibitors of integrin αvβ3 function and angiostatin);

(vi) vascular damaging agents, such as combretastatin A4 and compounds disclosed in International Patent Applications WO 99/02166, WO 00/40529, WO 00/41669, WO 01/92224, WO 02/04434 and WO 02/08213 (each of which is incorporated herein in its entirety);

(vii) antisense therapies, for example those which are directed to the targets listed above, such as ISIS 2503, an anti-ras antisense;

(viii) gene therapy approaches, including for example approaches to replace aberrant genes, such as aberrant p53 or aberrant BRCA1 or BRCA2, GDEPT (gene directed enzyme pro-drug therapy) approaches, such as those using cytosine deaminase, thymidine kinase or a bacterial nitroreductase enzyme and approaches to increase patient tolerance to chemotherapy or radiotherapy, such as multi-drug resistance gene therapy; and (ix) immunotherapeutic approaches, including for example ex vivo and in vivo approaches to increase the immunogenicity of patient tumour cells, such as transfection with cytokines, such as interleukin 2, interleukin 4 or granulocyte macrophage colony stimulating factor, approaches to decrease T-cell anergy, approaches using transfected immune cells, such as cytokine-transfected dendritic cells, approaches using cytokine-transfected tumour cell lines and approaches using anti-idiotypic antibodies.

A binding member of the invention and one or more of the above additional medicinal components may be used in the manufacture of a medicament. The medicament may be for separate or combined administration to an individual, and accordingly may comprise the binding member and the additional component as a combined preparation or as separate preparations. Separate preparations may be used to facilitate separate and sequential or simultaneous administration, and allow administration of the components by different routes e.g. oral and parenteral administration.

In accordance with the present invention, compositions provided may be administered to mammals. Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of binding member, the method of administration, the scheduling of administration and other factors known to medical practitioners. Prescription of treatment, e.g. decisions on dosage etc, is within the responsibility of general practitioners and other medical doctors and may depend on the severity of the symptoms and/or progression of a disease being treated. Appropriate doses of antibody are well known in the art [83, 84]. Specific dosages indicated herein or in the Physician's Desk Reference (2003) as appropriate for the type of medicament being administered may be used. A therapeutically effective amount or suitable dose of a binding member of the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody (e.g. whole antibody, fragment or diabody) and the nature of any detectable label or other molecule attached to the antibody. A typical antibody dose will be in the range 100 μg to 1 g for systemic applications, and 1 μg to 1 mg for topical applications. An initial higher loading dose, followed by one or more lower doses, may be administered. Typically, the antibody will be a whole antibody, e.g. the IgG1 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intra-venous administration. Treatment may be periodic, and the period between administrations is about two weeks or more, e.g. about three weeks or more, about four weeks or more, or about once a month. Treatment may be given before, and/or after surgery, and/or may be administered or applied directly at the anatomical site of surgical treatment.

Binding members of the invention may be used ex vivo to determine the level of CXCL13 in a sample as described herein. Such a method generally comprises contacting the sample with a binding member of the invention under conditions that allow binding of the binding member to CXCL13 and measuring the level of bound CXCL13 in the sample. The level of CXCL13 may be compared with a suitable standard or control.

The method may be used for the diagnosis or prognosis of a disease or condition in the individual from which the sample has been obtained, and for which CXCL13 levels are predictive. For example, the method may be used to diagnose or prognose disease severity in, rheumatoid arthritis, such a method comprises determining the level of CXCL13 in a suitable sample, e.g. a serum or synovial fluid sample, obtained from an individual suffering from or suspected to be suffering from rheumatoid arthritis. Elevated levels of CXCL13 compared to a control sample are indicative of disease, and there is a positive correlation between CXCL13 levels and disease severity.

EXAMPLES

Assay Materials and Methods
Materials
CHO Gqi5 cells:CHO K1 cells expressing G protein Gqi5 (SEQ ID NO: 19).
CHO Gqi5 hCXCR5 cells or CHO Gqi5 hCXCR5 c4.4 cells: CHO Gqi5 cells stably expressing human CXCR5 (SEQ ID NO: 17)
Minimal Essential Media (Gibco 31095)
1% Non Essential Amino Acids (Gibco 11140)
Assay Media for HTRF®cAMP Assay:
Minimal essential media (Gibco 31095) containing 0.5 mM 3-Isobutyl-1-methylxanthine (Sigma 17018)
1% Non essential amino acids (Gibco 11140) 0.1% BSA
cAMP-XL665 solution for HTRF assay: a solution comprising XL665 (an allophycocyanin dye, 80 kD in size, coupled directly to cAMP)
Conjugate Lysis Buffer for HTRF cAMP Assay
Anti-cAMP Europium Cryptate Solution for HTRF Assay
Hanks Balanced Salt Solution (Sigma H8264)
Assay Media for LANCE® cAMP Assay:
Hanks Balanced Salt solution (Sigma H8264) containing 5 mM HEPES pH7.4
0.5 mM 3-Isobutyl-1-methylxanthine (Sigma 17018) 0.1% BSA
Alexa Fluor®-647 anti-cAMP antibody for LANCE® cAMP assay: a cAMP specific antibody labelled with the dye Alexa Fluor®-647, formulated in 50 mM Tris HCl (pH7.8) salt solution, 0.9% sodium chloride, 0.1% BSA, 0.05% sodium azide (preservative).
LANCE® Detection Mix
Dulbecco's Modified Eagle's Medium (DMEM) (Invitrogen)
MEM-Non-essential Amino Acids without L-glutamine (Invitrogen)

CXCL13 Induced Ca2+ Release Assay Media:
Dulbecco's modified Eagle's medium (DMEM) containing 10% (v/v) heat inactivated foetal bovine serum (FBS) (Invitrogen)
1% (v/v) MEM-non-essential amino acids without L-glutamine (Invitrogen)
Dye-loading Solution for CXCL13 Induced Ca2+ Release Assay
Fluo-4 NW Dye Mix for CXCL13 Induced Ca2+ Release Assay
FLIPR Buffer:
125 mM NaCl
5 mM KCl
1 mM $MgCl_2$
1.5 mM $CaCl_2$
30 mM Hepes
2.5 mM probenecid (4-(dipropylsulfamoyl)benzoic acid) 5 mM glucose
1% (v/v) heat-inactivated FBS B300.19 hCXCR5 cells: A murine pre-B cell line stably transfected with human CXCR5

Culture Media for Chemotaxis Assay with B300.19 hCXCR5 Cells:
(RPMI-1640 Sigma, Cat# R0883), containing 10% foetal calf serum (FCS); 1% penicillin, streptomycin and glutamine (PSG); 1% sodium pyruvate; 1.5 µg/ml puramycin and 0.1% 2-β-mercaptoethanol.
Methods
CXCL13 Receptor-ligand Binding Assay (FMAT)

The CXCL13 receptor ligand binding assay measures the interaction between biotinylated human CXCL13 (Almac) and the CXCR5 receptor over-expressed on B300.19 cells (Almac) using Fluorescence Microvolume Assay Technology (FMAT) (Dietz et al 1996, Miraglia et al 1999, Mellentin-Michelotti et al. 1999). This assay may be used to screen crude scFv periplasmic extracts or purified scFv for inhibition of the CXCL13: CXCR5 interaction.

Selection outputs were screened as diluted crude scFv-containing periplasmic extracts prepared in 200 mM Tris buffer pH7.4, 0.5 M Sucrose. All dilutions of samples and reagents were carried out in Hanks Balanced Salt Solution (Sigma H8264) containing 0.025% Bovine Serum Albumin (BSA) and 0.01% Sodium Azide. Diluted samples (20 µL) were incubated with 1 nM biotinylated-human CXCL13, 25 ng/mL Streptavidin FMAT-Blue (Applied Biosystems 4362492) and B300.19 CXCR5 cells (4000 cells/well) for 2 hours at room temperature in a total assay volume of 50 µL in a 384 well clear-bottomed non-binding surface plate (Costar 3655). Total binding and non-specific binding (NSB) controls were set up using assay buffer or 3 nM final assay concentration anti-human CXCL13 monoclonal antibody (R&D Systems MAB801) respectively. Plates were read on the Applied Biosystems Cellular Detection System 8200 and data analysed using the Wang Goldman algorithm with gating of FL1<1600, size <15 and colour ratio <0.4.

% Specific binding was determined from the FL1 Total data using equation 1 where NSB FL1 Total is the mean value of the non specific binding control wells and Total binding FL1 Total is the mean value of the Total binding control wells.

$$\% \text{ specific binding} = \frac{(\text{Sample } FL1 \text{ Total} - NSB\ FL1 \text{ Total})}{(\text{Total binding } FL1 \text{ Total} - NSB\ FL1 \text{ Total})} \times 100 \qquad \text{Equation 1}$$

HTRF® cAMP Assay

3',5' cyclic adenosine monophosphate (cAMP) levels in cells are increased through the activation of the family of adenylyl cyclase enzymes, which catalyse conversion of adenosine triphosphate (ATP) to cAMP and pyrophosphate. Binding of CXCL13 to its G-protein coupled receptor CXCR5 can result in a down regulation of adenylyl cyclase activity and hence decrease in cellular cAMP levels through release of the G-protein subunit $G_{\alpha i}$, which inhibits adenylyl cyclase.

We used the HTRF® (Homogeneous Time-Resolved Fluorescence) cAMP assay kit (CisBio International 62AM4PEC) for determination of cellular cAMP levels. In the CXCL13 HTRF® cAMP Assay, CXCL13 mediated decreases in cAMP levels in CHO Gqi5 cells stably expressing CXCR5 are measured.

Co-stimulation of the cells with the adenylyl cyclase activator, NKH477 (Tocris Cookson 1603), a water-soluble forskolin derivative, is carried out to ensure the CXCL13 response is within the linear range of detection of the HTRF® cAMP assay kit.

This assay may be used to determine the potencies of scFvs for inhibition of the CXCL13 mediated modulation of cellular cAMP levels in CHO Gqi5 hCXCR5 cells.

ScFv samples, reagents and CHO Gqi5 hCXCR5 cells were prepared in Assay media (Minimal essential media (Gibco 31095) containing 0.5 mM 3-Isobutyl-1-methylxanthine (Sigma 17018), 1% Non essential amino acids (Gibco 11140) and 0.1% BSA) unless otherwise stated. CHO Gqi5 hCXCR5 cells were harvested from tissue culture flasks and resuspended at $1.2 \times 10^6$ cells/ml in Assay media. cAMP-XL665 and Anti-cAMP Europium Cryptate were reconstituted in distilled water according to the manufacturer's instructions (CisBio International)

ScFvs were pre-incubated with 4 nM human (SEQ ID NO: 14) or cynomolgus (SEQ ID NO: 16) CXCL13 (MEL cell derived) for 30 minutes at room temperature in a 384 well low volume plate (Costar 3676). 5 µl of the pre-incubated sample were transferred to the assay plate (Costar 3676), then 2.5 µl NKH477 and 2.5 µL CHO Gqi5 hCXCR5 cell suspension added to give a final reaction volume of 10 µl containing 0.5 µM NKH477 and 3000 cells/well. Each plate was set up with the following controls: NKH477 control (CHO Gqi5 hCXCR5 cells with 0.5 µM NKH477), CXCL13 control (2 nM CXCL13, 0.5 µM NKH477 and CHO Gqi5 hCXCR5 cells), basal cAMP control (CHO Gqi5 hCXCR5 cells only) and negative control (assay media only). CXCL13 and NKH477 titrations were also run in each experiment to ensure the concentrations used in the assay were within the $EC_{50}$-$EC_{85}$ range and hence within the linear range of detection of HTRF® cAMP assay kit. After addition of cells, plates were incubated for 30 minutes at room temperature, then the reactions stopped by addition of 5 µl cAMP-XL665 solution. This was followed by addition of 5 µl Conjugate Lysis buffer to the negative control wells or 5 µl Anti-cAMP Europium Cryptate solution to all other wells.

Assay plates were incubated for 2 hours at room temperature, prior to reading time resolved fluorescence at 620 nm and 665 nm emission wavelengths using an EnVision plate reader (Perkin Elmer).

Data were analysed by calculating Delta F % values for each sample. Delta F % was determined according to equation 2 where CXCL13 control Delta F % is the mean value of the CXCL13 control wells and NKH477 control Delta F % is the mean value of the NKH477 control wells.

$$\text{Delta } F\% = \frac{(\text{sample 665 nm/620 nm ratio value}) - (\text{negative control 665 nm/620 nm ratio value})}{(\text{negative control 665 nm/620 nm ratio value})} \times 100 \qquad \text{Equation 2}$$

% Delta F values were subsequently used to calculate % inhibition as described in equation 3.

$$\% \text{ inhibition} = \frac{(\text{Sample Delta } F\% - CXCL13 \text{ control Delta } F\%)}{(NKH477 \text{ control Delta } F\% - CXCL13 \text{ Control Delta } F\%)} \times 100 \qquad \text{Equation 3}$$

A titration of scFv concentrations was used in order to establish the clone potency as measured by $IC_{50}$ values in the assay. $IC_{50}$ values were determined using GraphPad Prism software by curve fitting using a four-parameter logistic equation (Equation 4).

$Y = \text{Bottom} + (\text{Top} - \text{Bottom})/(1 + 10^{((\log EC50 - X) * \text{HillSlope})})$  Equation 4:

X is the logarithm of concentration. Y is % inhibition

CXCL13 LANCE® cAMP Assay

The principle of the CXCL13 LANCE® cAMP Assay is comparable to that outlined for the CXCL13 HTRF® cAMP assay but cellular cAMP levels are measured using the LANCE® cAMP Assay kit (Perkin Elmer AD0263). The CXCL13 LANCE® cAMP Assay may be used to determine the potency of IgGs for inhibition of CXCL13 mediated decreases in cAMP levels in CHO Gqi5 hCXCR5 cells upon co-stimulation with NKH477.

All dilutions were carried out in Assay media (Hanks Balanced Salt solution (Sigma H8264) containing 5 mM HEPES pH7.4, 0.5 mM 3-Isobutyl-1-methylxanthine (Sigma 17018) and 0.1% BSA) unless otherwise stated. CHO Gqi5 hCXCR5 cells were harvested from tissue culture flasks and resuspended at $1.2 \times 10^6$ cells/ml in Assay media. Alexa Fluor®-647 anti-cAMP antibody was added to the cell suspension at a dilution of 1:100. LANCE® detection mix containing 1:2250 diluted Europium-W8044 Streptavidin and 1:750 fold diluted Biotin-cAMP was prepared at least 15 minutes prior to use as per the manufacturer's instructions. Europium-W8044 is a europium chelate with DCA (dichlorotriazinyl) reactive arm.

IgG samples were pre-incubated with 4 nM human (SEQ ID NO: 14) or cynomolgus (SEQ ID NO: 16) CXCL13 (MEL cell derived) and 2 µM NKH477 (Tocris Cookson 1603) for 1 hour at room temperature in a 384 well low volume plate (Costar 3676). 5 µL of the pre-incubated sample was transferred to a white Proxiplate Plus 384 well assay plate (Perkin Elmer Cat no. 6008280). Alexa Fluor®-647 anti-cAMP antibody/CHO Gqi5 hCXCR5 cell suspension (5 µL) was added to give a final reaction volume of 10 µL containing 1 µM NKH477, 3000 CHO Gqi5 hCXCR5 cells/well and 1:200 diluted Alexa Fluor®-647 anti-cAMP antibody. Each plate was set up with the following controls: NKH477 control (CHO Gqi5 hCXCR5 cells/Alexa Fluor®-647 anti-cAMP antibody and 1 µM NKH477) and CXCL13 control (2 nM CXCL13, 1 µM NKH477 and CHO Gqi5 hCXCR5 cells/ Alexa Fluor®-647 anti-cAMP antibody). CXCL13 and NKH477 titrations were also run in each experiment to ensure the concentrations used in the assay were within the $EC_{50}$-$EC_{85}$ range and hence within the linear range of detection of the LANCE® cAMP assay kit. After addition of the cell suspension plates were incubated for 30 minutes at room temperature, then the reactions stopped by addition of 10 µL LANCE® detection mix to all assay wells. Plates were incubated for 3 hours at room temperature then the emission at 665 nm wavelength determined using an EnVision plate reader (Perkin Elmer).

The 665 nm emission data was used to calculate % inhibition as described in equation 7, where CXCL13 control 665 nm emission is the mean value of the CXCL13 control wells and NKH477 control 665 nm emission is the mean value of the NKH477 control wells.

$$\% \text{ inhibition} = \frac{(\text{Sample 665 nm emission} - CXCL13 \text{ control 665 nm emission})}{(NKH477 \text{ control 665 nm emission} - CXCL13 \text{ control 665 nm emission})} \times 100 \qquad \text{Equation 7}$$

$IC_{50}$ values were determined using GraphPad Prism software by curve fitting using a four-parameter logistic equation (see Equation 4).

CHO Gqi5 hCXCR5 c4.4 CXCL13 Induced Ca2+ Release Assay

CHO Gqi5 hCXCR5 c4.4 cells were seeded in 96-well black-walled Poly-D-Lysine treated tissue culture assay plates (BD) at 1×105 cells/well. Cells were then cultured overnight in 100 μL assay media (Dulbecco's modified Eagle's medium (DMEM) (Invitrogen), 10% (v/v) heat inactivated foetal bovine serum (FBS) (Invitrogen), 1% (v/v) MEM-non-essential amino acids without L-glutamine (Invitrogen)) in a humidified atmosphere at 37° C. and 5% $CO_2$.

A no-wash FLIPR protocol was employed as follows, using a commercially available kit (Fluo-4 no wash Calcium Assay Kit F36206, Molecular Probes). Dye-loading solution was prepared by adding 10 mls of Assay buffer (20 mM HEPES in 1× Hanks Balanced salt solution) and 100 μl probenecid stock solution (250 mM in Assay buffer) to a single vial of Fluo-4 NW dye mix. Media was aspirated from cells, and 70 μl/well of dye-loading solution was added and incubated at 37° C. for 30 minutes, followed by 30 minutes at room temperature. During this incubation period, titrations of purified IgGs were prepared in FLIPR buffer (125 mM NaCl, 5 mM KCl, 1 mM $MgCl_2$, 1.5 mM $CaCl_2$, 30 mM Hepes, 2.5 mM probenecid, 5 mM glucose and 1% (v/v) heat-inactivated FBS) and pre-incubated with CXCL13 (100 nM final concentration) also in FLIPR buffer for 30 minutes at 37° C.

Following incubation, responses of labelled cells to CXCL13/IgG titrations were measured in the Fluorometric Imaging Plate Reader System (FLIPR). Fluorescence of the intracellular calcium-sensitive dye was assayed using a 470 to 495 nm excitation filter and 515 to 575 nm emission filter over a reading period of ×120 seconds.

Data was analysed by exporting the maximum peak height for each well to Excel (Microsoft). Inhibitor data was normalised to percentage of CXCL13-induced intracellular $Ca^{2+}$ using the response to CXCL13 in the absence of inhibitor, and subtracting the response to assay buffer alone. Further analysis was performed in Prism (GraphPad) where the data were plotted as percentage of the control response against log concentration of IgG. $IC_{50}$ values were calculated using Prism curve fitting software (Graphpad).

CXCL13 Fluorescence-linked Immunosorbent Assay (FLISA)

The CXCL13 FLISA measures the interaction between biotinylated human CXCL13 (Almac) coupled to a streptavidin bead and CXCL13 binding members in IgG format using Fluorescence Microvolume Assay Technology (Dietz et al 1996, Swartzman et al 1999). This assay may be used to determine the specificity of IgGs for biotinylated-human CXCL13 compared to related chemokine family members in a competition assay format.

Samples and reagents were diluted in Assay Buffer (Phosphate Buffered Saline with 0.1% BSA, 0.1% Tween-20 and 0.01% sodium azide). 0.25 nM biotinylated CXCL13 (Almac) was pre-incubated with 0.004% w/v 6-8 μm streptavidin coated polystyrene particles (Spherotec SVP-60-5) for 1 hour at room temperature. The beads were then centrifuged at 3000 rpm for 5 minutes, the supernatant discarded and the pellet resuspended in the original volume of assay buffer to give a 0.004% w/v bead/biotinylated humanCXCL13 mix. 10 μL competitor, assay buffer (total binding control) or excess humanCXCL13 (Non specific binding (NSB) control) was added to a 384 well clear-bottomed non-binding surface assay plate (Costar 3655). 10 μL 5 nM Goat anti-human (H+L) Alexa Fluor®-647 (Invitrogen A21445), 10 μL 0.31 nM Antibody 1 (germlined IgG) and 20 μL Bead/biotinylated CXCL13 mix were then added and the plates incubated for 4 hours at room temperature. FL1 signal was read on the Applied Biosystems Cellular Detection System 8200. Data was analysed using the Wang Goldman algorithm with gating of size 3-12, colour ratio <0.4, minimum count 20.

% Specific binding was determined from the FL1 data using equation 8, where NSB FL1 is the mean value of the non specific binding control wells and Total binding FL1 is the mean value of the Total binding control wells.

$$\% \text{ specific binding} = \frac{(\text{Sample } FL1 - NSB\ FL1)}{(\text{total binding } FL1 - NSB\ FL1)} \times 100 \qquad \text{Equation 8}$$

$IC_{50}$ values were determined using GraphPad Prism software by curve fitting using a four-parameter logistic equation (see Equation 4).

BIAcore Assessment of Antibody 1 (Germlined IgG) Interaction with Human and Cynomolgus CXCL13

Reagents:

CXCL13

Human CXCL13 (MEL cell expressed)

0.1 mg mL-1, expected average mass 9,694.53 Da, 10.31 μM. Dilution to 6 nM was 4 μL in 6,869 μL HBS-EP.

Cynomolgus CXCL13 (MEL cell expressed)

0.6 mg mL-1 diluted to 0.3 mg mL-1, expected average mass 9,670 Da, 31.02 μM). Dilution to 6 nM was 4 μL in 20,678 μL HBS-EP.

Immunoglobulins

Antibody 1 (Germlined)

4.42 mg mL-1 (for example 3a); 1.06 mg mL-1 (for example 3b)

Methodology for Example 3a

See example 3a for chip preparation.

For each experimental cycle (orientation 1) the Fc 2 Protein G' surface was used to capture 240-385 RUs Antibody 1(germlined $IgG_1$) by titrating a 0.5 μL mL-1 HBS-EP solution of Antibody 1(germlined $IgG_1$) at 5 μL min-1 for 2 minutes.

A specified dilution of either human or cynomolgus CXCL13 (0.25, 0.3125, 0.50, 0.625, 1.0, 1.25, 2.5, 5.0, 10.0 and 20.0 nM for Human CXCL13 or 0.125, 0.25, 0.50, 1.0, 2.0, 5.0, 10.0, 20.0 and 40.0 nM for cynomolgous CXCL13) in HBS-EP buffer was then flowed over the chip surface at a flow rate of 100 μL min-1 (association time of 2.5 minutes, dissociation for 10 minutes and regeneration with a 20 μL pulse of 10 mM Glycine pH 1.75 followed by a 20 μL pulse of 10 mM Glycine pH 1.50). Blank injections were made with the HBS-EP alone. All solutions were prepared and stored in polypropylene.

Methodology for Example 3b

Antibodies were diluted to 1.0 μg mL-1 in 10 mM acetate buffer pH 4.5. Standard amine linkage chemistry (using amine coupling kit BR-1000-50) was employed to create blank (Fc 1) and 500 RU surfaces of IgG on a CM3 chip (BIAcore, BR-1005-41, lot: 1160100 expiry April '07). The wash solution employed was Glycine pH 2.0.

Flow of human and cynomolgus CXCL13 over chip surfaces. A dilution series of each CXCL13 (0.10, 0.20, 0.30, 0.40, 0.50 and 0.60 nM) was constructed in HBS-EP buffer and flowed at 30 µL min-1 over all flow cells (association time of 4 minutes, dissociation for 10 minutes and regeneration with two 20 µL pulses of 10 mM Glycine pH 2.0). Blank injections were made with the same buffer. All solutions were prepared and stored in polypropylene.

Reformatting of scFv to IgG$_1$

Clones were converted from scFv to IgG format by subcloning the V$_H$ and V$_L$ domains into vectors expressing whole antibody heavy and light chains respectively. The V$_H$ domain was cloned into a vector (pEU15.1) containing the human heavy chain constant domains and regulatory elements to express whole IgG$_1$ heavy chain in mammalian cells. Similarly, the V$_L$ domain was cloned into a vector for the expression of the human light chain constant domains and regulatory elements to express whole IgG light chain in mammalian cells (pEU3.4 for kappa light chains, pEU4.4 for lambda). Vectors for the expression of heavy chains and light chains were originally described in Persic et al, 1997. Vectors have been engineered to permit episomal replication of the vectors.

To obtain IgGs, the heavy and light chain IgG expressing vectors were transfected into EBNA-HEK293 mammalian cells. IgGs were expressed and secreted into the serum-free medium. Harvests were pooled and filtered prior to purification. The IgG was purified using Protein A chromatography. Culture supernatants are loaded on a column of appropriate size of Ceramic Protein A (BioSepra) and washed with 50 mM Tris-HCl pH 8.0, 250 mM NaCl. Bound IgG was eluted from the column using 0.1 M Sodium Citrate (pH 3.0) and neutralised by the addition of Tris-HCl (pH 9.0). The eluted material was buffer exchanged into PBS using Nap10 columns (Amersham, #17-0854-02) and the concentration of IgG was determined spectrophotometrically using an extinction coefficient based on the amino acid sequence of the IgG (Mach 1992). The purified IgGs were analysed for aggregation or degradation using SEC-HPLC and by SDS-PAGE.

HTRF® Epitope Competition Assay

The HTRF® epitope competition assay may be used to determine competition between binding members for binding biotinylated CXCL13. Antibody molecules tested in this assay may for example be in scFv or IgG format.

The principles of the HTRF® technology are as described herein.

In an HTRF® epitope competition assay for determining the ability of a binding member to compete for binding to CXCL13 with an antibody scFv molecule having amino acid sequence SEQ ID NO: 11, a FRET complex is formed between cryptate labelled ScFv (SEQ ID NO: 11), biotinylated human CXCL13 and streptavidin XLent (streptavidin crosslinked with XL665, coupled under optimised conditions). An ScFv or IgG recognising the same (or possibly overlapping) epitope as the cryptate labelled ScFv will compete for binding to the biotinylated CXCL13 and thus reduce the assay signal.

All dilutions of samples and reagents are carried out in assay buffer (Phosphate Buffered Saline, 0.1% BSA, 0.4 M Potassium Fluoride). Biotinylated human CXCL13 (AlmacAlmac) and Streptavidin-XLent (CisBio International 611SAXLB) are pre-incubated at room temperature for 30 minutes. 10 µL of sample (scFv or IgG), assay buffer (total binding control) or 50× final assay concentration unlabelled IgG (to define non-specific binding (NSB)) are added to a 384 low volume plate (Costar 3676) followed by 5 µL of the pre-incubated Biotinylated CXCL13/Streptavidin XLent mix. Plates are incubated for 1 hour at room temperature after which 5 µL of cryptate labelled ScFv is added. Plates are incubated for 3 hours at room temperature prior to determination of time resolved fluorescence at 620 nm and 665 nm emission wavelengths using an EnVision plate reader (Perkin Elmer).

Optimal concentrations of CXCL13, streptavidin-XLent and cryptate labelled IgG may be titrated in to establish the concentration of each reagent that gives an appropriate assay signal.

Data is analysed by calculating Delta F% values for each sample (refer to equation 5).

$$\text{Delta } F\% = \frac{(\text{sample } 665 \text{ nm}/620 \text{ nm ratio}) - (NSB\ 665 \text{ nm}/620 \text{ nm ratio})}{(NSB\ 665 \text{ nm}/620 \text{ nm ratio})} \times 100 \quad \text{Equation 5}$$

Delta F % values are subsequently used to calculate % specific binding as described in equation 6, where NSB Delta F % is the mean value of the non specific binding control wells and Total binding Delta F % is the mean value of the Total binding control wells.

$$\% \text{ specific binding} = \frac{(\text{Sample Delta } F\% - NSB\ \text{Delta } F\%)}{(\text{Total binding Delta } F\% - NSB\ \text{Delta } F\%)} \times 100 \quad \text{Equation 6}$$

IC50 values are determined using GraphPad Prism software by curve fitting using a four-parameter logistic equation (see Equation 4).

$$Y = \text{Bottom} + (\text{Top} - \text{Bottom})/(1 + 10\string^((\text{Log } EC50 - X)*\text{HillSlope})) \quad \text{Equation 4:}$$

X is the logarithm of concentration. Y is % inhibition

B300.19 hCXCR5 Cell CXCL13 Driven Chemotaxis Assay

B300.19 hCXCR5 cells were adjusted to 5×10$^5$ cell/ml for at least 2 days prior to running the assay using culture media (RPMI-1640 Sigma, Cat# R0883) containing 10% foetal calf serum (FCS); 1% penicillin, streptomycin and glutamine (PSG); 1% sodium pyruvate; 1.5 µg/ml puramycin and 0.1% 2-β-mercaptoethanol) in a humidified atmosphere at 37° C., 5% CO$_2$. On the day of the assay, B300.19 hCXCR5 cells were counted and adjusted to 6×10$^6$ cell/ml after being spun down and washed once in buffer (RPMI-1640 (Sigma Cat# R0883) +0.35% BSA (Sigma Cat# A2153)).

Titrations of IgGs were made in assay buffer. The IgGs were pre-incubated with an ED80 concentration of CXCL13 for 30 min in a humidified atmosphere at 37° C., 5% CO$_2$.

Following this incubation period, 31 µl/well of the pre-incubated CXCL13 and IgG was transferred to the lower chamber of a chemotaxis plate (Receptor Technologies, Cat# 106-5) using reverse pipetting to avoid bubbles. The membrane filter was then applied over the wells securing each corner. 50 µl of the B300.19 hCXCR5 cells (6×10$^6$ cell/ml) were then dispensed into circled areas on the upper chamber of the chemotaxis filter. The lid was placed over the chemotaxis plate and incubated in a humidified atmosphere (37° C., 5% $CO_2$) for 2 hr.

Following the 2 hr incubation, the plates were removed from the incubator and washed to remove excess cells off the filter surface. This was done by pouring PBS over the membrane surface and using a cell scraper (Corning, Cat# 3011) to remove all excess cells/PBS. The chemotaxis plate was then centrifuged at 1500 rpm for 10 min, leaving the filter on.

Following the spin, the filter membrane was removed and the contents of the lower chamber of the chemotaxis plate were transferred to a 96-well polystyrene flat bottomed plate (Corning, Cat# 3598) (enzymatic plate) containing 80 µl/well of assay buffer and 15 µl/well of lysis buffer ($H_2O$+9% Triton-X). The plate was incubated for 1 hr in a humidified atmosphere (37° C., 5% $CO_2$).

Each plate was then subjected to a non-radioactive cytotoxicity assay measuring lactate dehydrogenase (LDH), a stable cytosolic enzyme, released on cell lysis. The assay provides a quantitative measure of cell number. The CytoTox 96 non-radioactive cytotoxicity assay (Promega Cat# G1780) consists of the following reagents: 5 vials Substrate Mix; 60 ml Assay Buffer; 25 µl LDH Positive Control (NOT USED); 3 ml Lysis Solution (10×) (NOT USED); 65 ml Stop Solution (1M Acetic Acid); 1 protocol. For the LDH Measurement the Assay Buffer was thawed; 12 ml was removed and the unused portion promptly stored at −20° C. A 37° C. water bath may be used to thaw the Assay Buffer. The 12 ml of Assay Buffer was warmed to room temperature (keep protected from light). The 12 ml of room temperature Assay Buffer was added to one bottle of Substrate Mix. This was inverted and shaken gently to dissolve the Substrate Mix.

One bottle will supply enough substrate for two 96-well plates. Once resuspended, the substrate should be protected from strong direct light and used immediately. 50 µl of reconstituted Substrate Mix was added to each well of the enzymatic assay plate containing lysed samples transferred from the chemotaxis assay plate. The plate was covered with foil or an opaque box to protect it from light and incubated for 30 minutes at room temperature. 50 µl of Stop Solution was added to each well. Any large bubbles were popped using a syringe needle, and the absorbance at 490 or 492 nm within 1 hour after the addition of Stop Solution was recorded.

Data was loaded into the GraphPad Prism 4 and this software generated the IC50 values based on the dose response curves generated.

Human Tonisillar B Cell CXCL13 Driven Chemotaxis Assay

Human tonsils were obtained after tonsillectomy surgery from patients under the approval of local ethics committees. Samples were shipped in RPMI-1640 (Sigma: R0883) media containing 10% Foetal Calf Serum, 1% Penicillin (10,000 units/ml)+Streptomycin (10 mg/ml)+Glutamine (200 mM) solution (Sigma: G1146) to gives a final concentration of 100 Units/ml Penicillin+0.1 mg/ml Streptomycin+2 mM Glutamine solution, 100 µg/ml Gentamycin (Sigma: G1522), 0.1% Beta mercaptoethanol (Gibco: 31350-010), 1% Sodium Pyruvate (Sigma: S8636), 1% Non-Essential Amino Acids (Gibco: 11140-035).

Primary tonsillar B cells were isolated from the tonsil tissue using a cell dissociation sieve (60 mesh size) (Sigma: CD1). The cell suspension was then washed by centrifugation at 300 g (1500 rpm) for 5 mins. The supernatant was discarded and the cell pellet resuspended in a total of 20 ml of cold tissue culture medium. The cell suspension was layered over 20 ml of Ficoll hypaque (Lymphoprep) (Axis Shields: 1114544) and centrifuged at 2000 rpm for 15 mins to remove dead cells, cell debris and erythrocytes. The cells at the interface of lymphoprep and tissue culture medium were removed with a plastic pasteur pipette and transferred to a 15 ml centrifuge tube. The cell suspension was made up to a volume of 15 ml with cold tissue culture medium and centrifuged at 1500 rpm for 5 mins. The supernatant was discarded and the cell pellet resuspended in 10 ml of cold tissue culture medium. A viable cell count is performed using a coulter counter. Cells were adjusted to a concentration of $5\times10^6$ cells per ml and cultured overnight with 1 µg/ml LPS approximately 20 hrs. Following the incubation the tonsillar cells were adjusted to $1\times10^7$ cell/ml after being spun down and washed once in buffer (RPMI-1640 (Sigma Cat# R0883)+ 0.35% BSA (Sigma Cat# A2153)). The chemotaxis assay was then carried out as previously described for the B300.19 hCXCR5 cells.

Binding of Native hCXCL13 to Antibody 1 (Germlined $IgG_1$) in an ELISA

Whole blood from was collected from into a heparinised container under the approval of local ethics committees. Blood was slowly layered over an equal volume of Lymphoprep using a stripette into a 50 ml Falcon tube. The tubes were spun at 2000 rpm for 25 min at room temperature with the brake off.

The lymphocyte layer was removed using a Pasteur pipette and transferred into a fresh Fisher 50 ml tube. The cells were then washed with pre-warmed RPMI-1640 (Sigma: R0883) media. The cells were then washed by centrifugation at 1500 rpm for 10 min with the brake on. The supernatant was discarded and the cells were then washed a twice more by centrifugation using RPMI at 1500 rpm for 10 min with the brake on. For the final wash, the pellet was resuspended in 50 ml of RPMI and a 200 µl sample removed for counting using the Coulter Counter.

Following the final wash, the cells were resuspended in the appropriate amount of culture media (RPMI-1640 (Sigma: R0883) media containing 10% Foetal Calf Serum, 1% Penicillin (10,000 units/ml)+Streptomycin (10 mg/ml)+ Glutamine (200 mM) solution (Sigma: G1146) to gives a final concentration of 100 Units/ml Penicillin+0.1 mg/ml Streptomycin+2 mM Glutamine) to obtain a cell concentration of $3.3\times10^6$ cell/ml.

Cells were then dispensed into 6-well polystyrene tissue culture plates, 3 ml per well. This gives a final cell number of approximately $1\times10^7$ cell/well. As many plates as possible were set up for the 6-day stimulation.

Plates were then incubated at 37° C., 5% $CO_2$ for 3-4 hours. During this incubation the monocytes should stick to the bottom of the wells leaving other cell populations in suspension.

Following the incubation, the 3 ml of culture media containing non-adherent cells was gently drawn out of each well and discarded leaving just the adherent monocytes on the base of each well. To each well of each plate, 3 ml of fresh culture media was added. The following stimulants were added:

Human M-CSF (R&D Systems: 216-MC-025) to obtain a final concentration of 50 ng/ml+human IL-4 (R&D Systems: 204-MC-025) to obtain a final concentration of 25 ng/ml.

1 well was left unstimulated as a control, containing media alone.

Following the 6-day stimulation, at 37° C., 5% $CO_2$, LPS was added overnight to all stimulated wells to a final concentration of 1 µg/ml. After the overnight stimulation with LPS, the supernatants were taken out of each well using a stripette. All supernatant was pooled and then dispensed into 15 ml tubes (10 ml per tube). ~500 µl was collected into an eppendorff tube for quantification by ELISA. CXCL13 Quantification by ELISA was carried out according to the manufacturers instructions.

(R&D systems: Quantikine Human CXCL13/BLC/BCA-1 Immunoassay. Cat. N°: DCX130)

The supernatant containing native CXCL13 was then purified on a cation exchange resin and dialysed into PBS and requantified using by ELISA.

To show binding of the native CXCL13 to Antibody 1 (germlined IgG$_1$), maxi-sorp high binding 96-well plates were coated with CAZ-1040 (5 µg/ml 200 µl per well). Also, within the ELISA kit, plates were provided coated with unspecified anti-CXCL-13 antibody. The purified native CXCL13 was then added to both Antibody 1-coated and kit supplied plates. The ELISA was then carried out according to manufacturers instructions (R&D systems: Quantikine Human CXCL13/BLC/BCA-1 Immunoassay. Cat. N°: DCX130).

Antibody 1 binds to both native CXCL13 and recombinant CXCL13 (standards provided in kit) with equivalent concentrations of ligands giving an equivalent signal in the assay.

Perturbation of H/D Exchange Rate of CXCL-13 by Binding Member

CXCL13 was used at 0.5 mg/ml in 50 mM Tris.HCl pH 7.4, 150 mM NaCl. Antibody was used at 10.6 mg/ml in PBS (1.54 mM KH2PO4, 2.71 mM Na2HPO4, 155 mM NaCl pH7.2). Antibody was coupled to POROS AL resin (Applied Biosystems) according to the manufacturer's instructions to prepare a 100 µl column which was kept at 1° C.

The column was washed in 50 mM Tris.HCl pH7.5, 150 mM NaCl prepared in 75% D2O. CXCL13 was diluted in buffer prepared with 75% D2O to 0.125 mg/ml and incubated for 150, 500, 1500 and 5000 s before injection onto the antibody column. The column was quickly washed with 0.2 ml buffer in H2O and then incubated for the same period of time i.e. the sample that was exchanged into D2O for 150 s was exchanged back to H2O for 150 s and similarly for the samples at 500, 1500 and 5000 s. The different time points were eluted by injecting first 80 µl and then 40 µl 0.8% formic acid. The latter 40 µl was collected and 20 µl of 2 M urea, 1 M TCEP pH3 at 1° C. added. The whole mixture was injected onto a 100 µl column containing pepsin to digest the protein into peptides that were separated by rpHPLC using a gradient of acetonitrile from 12-28.5% and the masses determined on both a Thermo Finnigan LCQ electrospray mass spectrometer and a Micromass Q-TOF mass spectrometer. The SEQUEST software program (Thermo Finnigan San Jose, Calif.) was used to identify sequences of the parent peptide ions.

The effect of the antibody on the rate of exchange of different parts of CXCL13 was determined essentially as described above, with the following exceptions: the CXCL13 was first diluted to 0.125 mg/ml in H2O containing buffer, then injected onto the column which had been pre-washed with 50 mM Tris.HCl pH7.5, 150 mM NaCl prepared in H2O. After binding, the column was washed with 50 mM Tris.HCl pH7.5, 150 mM NaCl prepared in H2O and then incubated with 50 mM Tris.HCl pH7.5, 150 mM NaCl prepared in 75% D2O for 150, 500, 1500 and 5000 s before being exchanged back into H2O and treated as above.

Example 1

Antibody Lead Isolation

Human spleen cDNA was used as a template to PCR the open reading frame of human CXCL13. This was cloned into a mammalian expression vector (pEV3) for stable transfection of MEL cells. The highest CXCL13-expressing clonal MEL cell line was identified by western blot of cell culture supernatants using a commercially available anti-CXCL13 antibody. Recombinant CXCL13 was purified from the culture medium of MEL cells expressing the protein by adjusting the pH to 6 and then loading it onto a cation exchange column. CXCL13 was eluted in a MES buffer at pH6 containing 1M NaCl. The sample was loaded directly onto a Resource rpc column and eluted with a gradient of up to 90% acetonitrile in 0.1% TFA. Fractions containing CXCL13 were pooled, concentrated and purified by chromatography on a Superdex75 column to generate material of >95% purity. The purified protein was analysed by SDS-PAGE and LCMS and shown to have a mass of 9690 Da.

1.1 Selections from the scFv Phage Display Library

Large single chain Fv (scFv) human antibody libraries cloned into a phagemid vector based on filamentous phage M13 were used for selections (Vaughan 1996, Hutchings 2001). Anti-CXCL13 specific scFv antibodies were isolated from the phage display libraries using a series of selection cycles on chemically synthesised biotinylated human CXCL13 (Almac) essentially as previously described (Vaughan 1996). In brief purified phage in PBS-Marvel (3% w/v) were allowed bind to biotinylated human CXCL13 in solution for 1 h. ScFv-phage bound to antigen were then captured on streptavidin-coated paramagnetic beads (Dynabeads® M-280) following the manufacturer's recommendations. Unbound phage particles were removed by a series of wash cycles using PBS-Tween (0.1% v/v) and PBS. Bound phage particles were eluted, infected into bacteria and rescued for the next round of selection (Vaughan 1996).

A representative number of individual clones from the second round of selections was grown up in 96-well plates. ScFvs were expressed in the bacterial periplasm and screened for their ability to inhibit binding of biotinylated human CXCL13 (Almac) to its receptor CXCR5 expressed on B300.19 hCXCR5 cells using Fluorescence Microvolume Assay Technology (FMAT). ScFvs which showed a significant inhibitory effect as crude periprep samples on the CXCL13: CXCR5 interaction in the assay were subjected to DNA sequencing (Vaughan 1996, Osbourn 1996).

Unique scFvs were expressed again in bacteria and purified by affinity chromatography (as described in Bannister 2006). IC50 values were determined by testing dilution series of purified scFvs in a HTRF cAMP (3',5' cyclic adenosine monophosphate) assay against human and cynomolgus (cyno) non-human primate CXCL13 (both MEL cell derived).

1.2 Determination of Functional Activity. Inhibition of CXCL13 Stimulated Cyclic AMP Formation In the CXCL13 HTRF® cAMP assay inhibition by lead scFvs of CXCL13 mediated decreases in cAMP levels upon co-stimulation of CHO Gqi5 hCXCR5 cells with the adenylyl cyclase activator NKH477 (0.5 µM), was measured. IC$_{50}$ values were determined against final reaction concentrations of 2 nM Human CXCL13 (MEL cell derived) or 2 nM cynomolgus CXCL13 (MEL cell derived) (see Table 1). For details of the assay method, refer to the section "Assay Materials and Methods".

TABLE 1

Examples of Antibody 1 scFv (non-germlined) potencies against human CXCL13 (Average IC$_{50}$ ± standard deviation, n number) or cynomolgus CXCL13 (n = 1 data only) in the HTRF ® CXCL13 cAMP Assay

| Clone name | Human CXCL13 IC$_{50}$ nM ± SD (n number) | Cyno CXCL13 IC$_{50}$ nM (n = 1) |
|---|---|---|
| Antibody 1 (non-germlined) | 5 ± 1 (n = 3) | 3 |

1.3 Potency of IgGs in the LANCE® CXCL13 cAMP Assay

Activity of clones reformatted to IgG$_1$ (see Materials and Methods) was determined in the LANCE® cAMP assay. The principle of this assay is comparable to that of the HTRF® cAMP assay but uses the LANCE® cAMP assay kit (Perkin Elmer) for determination of cellular cAMP levels. For details of the assay method, see the section "Assay Materials and Methods". In the CXCL13 LANCE® cAMP Assay IC$_{50}$ values for IgG inhibition of MEL cell derived CXCL13 (2 nM human CXCL13 or 2 nM cyno CXCL13) mediated decreases in cAMP levels upon co-stimulation of CHO Gqi5 hCXCR5 cells with the adenylyl cyclase activator NKH477 (1 µM), were determined (for example data see Table 2).

TABLE 2

Examples of Antibody 1 IgG (non-germlined) potencies against MEL cell derived human CXCL13 (Average IC50 ± standard deviation, n number) or cynomolgus CXCL13 (n = 6 data) in the LANCE ® CXCL13 cAMP Assay.

| | Clone name | |
|---|---|---|
| | Human CXCL13 IC$_{50}$ nM ± SD (n number) | Cyno CXCL13 IC$_{50}$ nM ± SD (n number) |
| Antibody 1 (IgG non-germlined) | 1.4 ± 0.5 (n = 10) | 0.3 ± 0.1 (n = 6) |

1.4 Inhibition of CXCL13 Induced Chemotaxis in B300.19 Cells Expressing Recombinant CXCR5

IgGs were tested in a chemotaxis assay using B300.19 hCXCR5 cells, a murine pre-B cell line that has been transfected with human recombinant CXCR5. IgGs were titrated against a concentration of unglycosylated human CXCL13 which gave an approximately ED80 response (12.32 nM) The table below illustrates IC50 values (nM)±SEM for Antibody 1 IgG (non-germlined). Each IgG was tested at least 3 times.

TABLE 3

Example of IC50 values (nM) ± SEM for Antibody 1 IgG (non-germlined) in the B300.19 hCXCR5 chemotaxis assay.

| IgG | IC50 (nM ± SEM) Unglycosylated hCXCL13 |
|---|---|
| Antibody 1 (non-germlined) | 5.26 ± 0.62 |

1.5 Inhibition of CXCL13 Induced Calcium Release

IgG activity on CXCL13 induced calcium release was evaluated using a CHO cell line transfected with the G-protein Gqi5 and human CXCR5. Stimulation of these cells with human CXCL13 gives rise to increases in cytoplasmic Ca$^{2+}$ in a concentration dependent manner by inducing release from intracellular stores and influx from extracellular media. This can be measured using calcium-sensitive dyes in a Fluorescence Imaging Plate Reader (FLIPR). In this assay, the inhibitory activity, as determined by their IC$_{50}$ values, of anti-CXCL13 IgG was determined against 100 nM human CXCL13 (MEL cell derived). The IgG potencies obtained for Antibody 1 (non-germlined) are shown in Table 4. Positive assay controls were included in all assays. For full details of the assay method see "Assay materials and methods".

TABLE 4

Antibody 1 IgG (non-germlined) potency in the CXCL13 mediated CHO Gqi5 hCXCR5 Ca$^{2+}$ release assay (Average IC$_{50}$ ± standard deviation)

| Clone name | IgG IC$_{50}$ nM (n = 8) |
|---|---|
| Antibody 1 (non-germlined) | 17.1 ± 11.2 |

Example 2

Antibody Germlining 2.1 Antibody Germlining

The amino acid sequences of the VH and VL domains of the anti-CXCL13 antibodies were aligned to the known human germline sequences in the VBASE database (Tomlinson 1997), and the closest germline was identified by sequence similarity. For the VH domains of Antibody 1 this was VH3-23. For the VL domains it was VK1 L12. Without considering the Vernier residues (Foote 1992), which were left unchanged, there were 8 changes in the framework regions of the VH domain and 3 changes in the VL domain all of which were reverted to the indicated germline sequence by standard site-directed mutagenesis techniques using appropriate mutagenic primers (Q1E, V5L, R16G, V23A, G24A, H39Q, G83R and R105Q in the VH and I15V, A58V and D70E in the VL) to form the germlined 2.2 Potency of Germlined Antibody 1 IgG in the LANCE® cAMP Assay The potencies of the germlined and parent (non-germlined) Antibody 1 IgG, for inhibition of human or cyno CXCL13 (MEL cell derived) modulation of cAMP levels in CHO Gqi5 hCXCR5 cells, were compared using the LANCE® CXCL13 cAMP Assay as outlined in section 1.3. IC$_{50}$ values are shown in Table 5.

TABLE 5

Potency of germlined and parent Antibody 1 IgG against human or cynomolgus CXCL13 (Average IC$_{50}$ ± Standard deviation, n number) in the LANCE ® CXCL13 cAMP Assay

| | Clones | |
|---|---|---|
| | Human CXCL13 IC$_{50}$ nM (n number) | Cyno CXCL13 IC$_{50}$ nM (n number) |
| Antibody 1 Parent | 1.4 ± 0.5 (n = 10) | 0.3 ± 0.1 (n = 6) |
| Antibody 1 Germlined | 1.6 ± 0.3 (n = 4) | 0.3 ± 0.1 (n = 4) |

The parent and germlined Antibody 1 IgG showed comparable activities in this assay.

2.3 Potency of Germlined Antibody 1 IgG in the Chemotaxis Assay Using B300.19 hCXCR5 Cells Fully germlined Antibody 1 IgGs were tested in the chemotaxis assay using B300.19 hCXCR5 cells. IgGs were titrated against ED80 concentrations of unglycosylated and glycosylated human and glycosylated cyno CXCL13. The results are shown in Table 6 below as IC$_{50}$ values (nM)±SEM. IgGs were tested at least 3 times.

TABLE 6

Example of $IC_{50}$ values (nM) ± SEM for germlined Antibody 1 IgG in the B300.19 hCXCR5 chemotaxis assay.

| | $IC_{50}$ nM ± SEM | | |
|---|---|---|---|
| | Human CXCL13 | | Cyno CXCL13 |
| IgG | Unglycosylated | Glycosylated | Glycosylated |
| Antibody 1 (germlined) | 6.22 ± 0.7 | 3.94 ± 1.5 | 4.53 ± 0.6 |

2.4 Inhibition of CXCL13 Induced Calcium Release by Germlined Antibody 1 IgG

The potency of the germlined and parent (non-germlined) Antibody 1 IgG, was compared in the FLIPR assay as outlined in section 1.5.

TABLE 7

Examples of IgG potencies in the CXCL13 mediated CHO Gqi5 hCXCR5 c4.4 $Ca^{2+}$ release assay (Average $IC_{50}$ ± Standard deviation, n number).

| Clone name | IgG $IC_{50}$ nM ± SD |
|---|---|
| Antibody 1 Parent | 17.1 ± 11.2 (n = 8) |
| Antibody 1 Germlined | 10.4 ± 6.3 (n = 7) |

2.5 Specificity of Germlined Antibody 1 IgG for Human CXCL13

Specificity of the germlined Antibody 1 $IgG_1$ for human CXCL13 (MEL cell derived) over other members of the CXC family of chemokines was determined using the CXCL13 FLISA (Fluorescence linked immunosorbent assay). In this assay the chemokines CXCL3 (R&D Systems), CXCL5 (R&D Systems), CXCL6 (R&D Systems), CXCL8 (R&D Systems), CXCL10 (R&D Systems) and CXCL12 (Peprotech) were tested for competition with biotinylated human CXCL13 (Almac) immobilised on a streptavidin bead for binding to germlined Antibody 1 $IgG_1$. The biotinylated human CXCL13 antibody-binding interaction was detected with a fluorescently tagged anti-human IgG antibody using Fluorescence Microvolume assay Technology (refer to "Assay Materials and Methods" for details). Results are shown in Table 8. Standard chemokine names (Zlotnik and Yoshie, 2000) are given together with their most commonly used synonym.

TABLE 8

Examples of chemokine inhibition of biotinylated-human CXCL13 binding to germlined Antibody 1 $IgG_1$ (n = 1 data only)

| Chemokine | Inhibition of Antibody 1 $IgG_1$ germlined binding to biotinylated human CXCL13 $IC_{50}$ (nM) |
|---|---|
| Human CXCL13 (MEL cell derived) | 0.2 |
| Cyno CXCL13 (MEL cell derived) | 0.8 |
| CXCL3 (GROγ) | >1 μM |
| CXCL5 (ENA-78) | >1 μM |
| CXCL6 (GCP-2) | >1 μM |
| CXCL8 (IL-8) | >1 μM |
| CXCL10 (IP10) | >1 μM |
| CXCL12 (SDF-1α) | >1 μM |

Human CXCL13 and cynomolgus CXCL13 competed with biotinylated human CXCL13 for binding to the germ- lined Antibody 1 $IgG_1$. None of the other chemokines tested showed inhibition of the biotinylated human CXCL13 Antibody 1 IgG binding interaction up to a concentration of 1 μM.

Example 3a

Affinity of Antibodies for Human and Cyno CXCL13

3.1 Determination of Antibody Affinity by BIAcore Measurements

Determination of kinetic binding parameters was done by surface plasmon resonance (SPR) using the BIAcore 2000 optical biosensor (BIAcore AB, Upsalla, Sweden) essentially as described by Karlsson et al, 1991. See also Assay Materials and Methods section.

Orientation 1.

Standard amine linkage chemistry was employed to create blank and 265 RU surfaces of Protein G' (Sigma P4689) on Flow cells (Fc) 1 and 2, respectively, of a normalized CM5 chip (BIAcore, BR-1000-14). This Fc 2 Protein G' surface was used to capture 240-385 RUs Antibody 1(germlined $IgG_1$).

TABLE 9

| Flow cell (Fc) | Ligand | Response 1 (Bound RU) |
|---|---|---|
| 1 | Blank (HBS-EP) | n/a |
| 2 | Protein G' (diluted to 20 μg mL − 1 in 10 mM acetate buffer pH 4.5) | 265 |

Dilutions of human and cynomolgus CXCL13 (in HBS-EP buffer) were then flowed over the chip surface at a flow rate of 100 μL min-1.

1:1 Langmuir with mass transport limitation model fits to Fc 2-1 data

Fitting conditions (performed on BIAevaluation 3.2):

Double blank subtracted (blank flow cell subtracted from IgG flow cell data and a blank injection (0.01 M HEPES pH 7.4, 0.15 M NaCl, 3 mM EDTA, 0.005% v/v Surfactant P20, HBS-EP) was subtracted from the rest of data set). Bulk RI contributions were all set to zero locally.

Using the 1:1 Langmuir with mass transport limitation model, HBS-EP subtraction and RI set to zero, the following parameters were obtained, based on the 0.25-20 nM human CXCL13 curves (10 concentrations).

TABLE 10a

| | ka (M−1 s−1) | kd (s−1) | Rmax (RU) | $K_D$ (M) | $Chi^2$ |
|---|---|---|---|---|---|
| 238 RUs Antibody 1 (germlined, | 2.13e7 | 6.84e−4 | 37.2 | 3.22e−11 | 0.425 |
| 385 RUs Antibody 1 (germlined, | 1.42e7 | 7.15e−4 | 58.2 | 5.04e−11 | 0.529 |
| 347 RUs Antibody 1 (germlined, | 1.76e7 | 7.36e−4 | 52.9 | 4.17e−11 | 0.690 |

TABLE 10b

|  | ka (M−1 s−1) | kd (s−1) | $K_D$ (M) |
|---|---|---|---|
| Average values from the 3 experiments | 1.77e7 | 7.12e-4 | 4.14e-11 |

Using the 1:1 Langmuir with mass transport limitation model, HBS-EP subtraction and RI set to zero; the following parameters were obtained for the IgG, based on the 0.125-40 nM cyno CXCL13 curves (12 and 9 concentrations).

TABLE 11

|  | ka (M−1 s−1) | kd (s−1) | Rmax (RU) | $K_D$ (M) | $Chi^2$ |
|---|---|---|---|---|---|
| 303 RUs Antibody 1 (germlined, | 1.97e7 | 6.50e-4 | 49.6 | 3.30e-11 | 1.35 |
| 296 RUs Antibody 1 (germlined, | 2.05e7 | 5.99e-4 | 47.2 | 2.91e-11 | 0.683 |

TABLE 11b

|  | ka (M−1 s−1) | kd (s−1) | $K_D$ (M) |
|---|---|---|---|
| Average values from the 2 experiments | 2.01e7 | 6.25e-4 | 3.11e-11 |

The cyno CXCL13 fit for Antibody 1 (germlined) gives a very similar $K_D$ value to the human CXCL13 suggesting that the affinity for each variant is very similar.

Orientation 2.

Standard amine linkage chemistry was employed to create blank (Fc 1) and 228 and 303 RU surfaces of Streptavidin (Perbio/Pierce 21125) on Flow cells (Fc) 2 and 3, respectively, of a normalized CM5 chip (BIAcore, BR-1000-14). This Fc 3 streptavidin surface was used to capture 28 RUs human CXCL13 biotinylated near the C-terminus (Almac custom synthesis).

Dilutions of Size Exclusion Chromatography monomerized Fab fragments of Antibody 1 (diluted in HBS-EP buffer) were then flowed over the chip surface at a flow rate of 30 μL min-1.

1:1 Langmuir model fits to Fc 3-1 data

Fitting conditions (performed on BIAevaluation 3.2):

Double blank subtracted (blank flow cell subtracted from IgG flow cell data and a blank injection (0.01 M HEPES pH 7.4, 0.15 M NaCl, 3 mM EDTA, 0.005% v/v Surfactant P20, HBS-EP) was subtracted from the rest of data set). Bulk RI contributions were all set to zero locally.

Using the 1:1 Langmuir with mass transport limitation model, HBS-EP subtraction and RI set to zero, the following parameters were obtained, based on the 0.065-2.105 nM Antibody 1 (germlined $IgG_1$) Fab curves (6 concentrations).

TABLE 13

|  | ka (M−1 s−1) | kd (s−1) | Rmax (RU) | $K_D$ (M) | $Chi^2$ |
|---|---|---|---|---|---|
| 28 RUs human CXCL13 | 8.98e6 | 1.66e-3 | 41.6 | 1.85e-10 | 0.394 |

Example 3b

Affinity of Antibodies for Human CXCL13

Prior to the more comprehensive data set out in Example 3a, initial affinity data (n=1) was determined using a lower spread of CXCL-13 concentrations as described below. See also Assay Materials and Methods section.

3.1b Determination of Antibody Affinity by BIAcore Measurements

Determination of kinetic binding parameters was done by surface plasmon resonance (SPR) using the BIAcore 2000 optical biosensor (BIAcore AB, Upsalla, Sweden) essentially as described by Karlsson et al, 1991.

Standard amine linkage chemistry was employed to create blank (Fc 1) and 500 RU surfaces of Antibody 1(germlined $IgG_1$) diluted in 10 mM acetate buffer pH 4.5 on a CM3 chip (BIAcore, BR-1005-41).

TABLE 14

| Flow cell (Fc) | Ligand | Response 1 (Bound RU) | Aimed for (RU) |
|---|---|---|---|
| 1 | Blank (HBS-EP) | n/a | — |
| 2 | Antibody 1 (germlined) | 579.9 | 500 |

Dilutions of human and cynomolgus CXCL13 were then flowed over the chip surface.

Langmuir fits to Fc 2-1 and 3-1 data

Fitting conditions (performed on BIAevaluation 3.2):

Double blank subtracted (blank flow cell subtracted from IgG flow cell data and a blank injection (0.01 M HEPES pH 7.4, 0.15 M NaCl, 3 mM EDTA, 0.005% v/v Surfactant P20, HBS-EP) was subtracted from rest of data set). Bulk RI contribution all set to zero locally.

Using the 1:1 Langmuir model, HBS-EP subtraction and RI set to zero, the following parameters were obtained, based on the 0.10-0.60 nM human CXCL13 curves.

TABLE 15

|  | ka (M-1 s-1) | kd (s−1) | Rmax (RU) | $K_D$ (M) | $Chi^2$ |
|---|---|---|---|---|---|
| 579 RUs Antibody 1 (germlined) | 2.02e6 | 5.24e-4 | 54.2 | 2.59e-10 | 0.183 |

Using the 1:1 Langmuir model, HBS-EP subtraction and RI set to zero; the following parameters were obtained for each IgG, based on the 0.10-0.60 nM cyno CXCL13 curves.

TABLE 16

|  | ka (M-1 s-1) | kd (s−1) | Rmax (RU) | $K_D$ (M) | $Chi^2$ |
|---|---|---|---|---|---|
| 579 RUs Antibody 1 (germlined) | 3.63e6 | 1.04e-4 | 38 | 2.85e-10 | 0.161 |

Example 4

Inhibition of CXCL13 Induced Chemotaxis of Primary B Cells 4.1 Inhibition of CXCL13 Induced Chemotaxis of Primary Lymphocytes Isolated from Mouse Spleen Primary lymphocytes were freshly isolated from mice spleens and cultured overnight with LPS. The cells were then used in a chemotaxis assay stimulated by either commercially available murine CXCL13 (R&D Systems)or human CXCL13 (MEL cell derived). $IC_{50}$ data (nM) for Antibody 1 IgG (non-germlined)is shown in Table 12 below (n=1 and n=2 data only).

TABLE 12

| IgG | $IC_{50}$ (nM) | |
| --- | --- | --- |
| | Human CXCL13 | Mouse CXCL13 |
| Antibody 1 IgG (non-germlined) | 29.76 (n = 2) [27.3, n = 1] | Not measurable |

Example 5

Human Tonisillar B Cell CXCL13 Driven Chemotaxis Assay 1.4 Inhibition of CXCL13 Induced Chemotaxis in Human Tonsillar B Cells Primary tonsillar B cells were freshly isolated from human tonsils and cultured overnight with LPS. The cells were then used in a chemotaxis assay using human non-glycosylated CXCL13 (ABL—MEL cell derived) at an ED80 concentration (100 nM). For details of assay method, see the section "Assay Materials and Methods". IC50 data (nM) for Antibody 1 (germlined $IgG_1$) is shown in Table 17 (n=4 data).

TABLE 17

| IgG | Antibody 1 (germlined $IgG_1$) |
| --- | --- |
| IC50 (nM) | 9.59 +/- 1.6 |

Example 6

Binding of Native hCXCL13 to Antibody 1 (Germlined $IgG_1$) in an ELISA

As set out in the section "Assay Materials and Methods", Antibody 1 (germlined $IgG_1$) binds to both native CXCL13 and recombinant CXCL13 with equivalent concentrations of ligands giving an equivalent signal in the assay.

Example 7

Perturbation of H/D Exchange Rate of CXCL-13 by Antibody 1 (Germlined $IgG_1$)

In the first experiment CXCL13 was exchanged for $D_2O$ in solution and then bound to antibody 1 (IgG1) immobilised on a column. It was then back exchanged in $H_2O$ while still bound to the antibody column, resulting in the epitope being protected during the back exchange reaction and consequently labelled with deuterons. In the second experiment the CXCL13 was first bound to antibody 1 on the column, then labelled with D2O and finally exchanged back into H2O while still bound to the column, such that no parts of the CXCL13 were labelled with deuterons. The difference in masses of peptides between the two experiments were then determined. The difference in deuteration levels between the two experiments is a measure of the retardation of exchange when bound to antibody. A detailed method for this protocol is provided in the Materials and Methods section.

Human CXCL13 expressed in MEL cells was used in this study with the sequence shown in SEQ ID NO 14.

The region that showed the greatest perturbation in the rate of H/D exchange was between amino acids 31-42 of human CXCL-13 (SEQ ID No. 20).

At pH 7 the rate of exchange is very fast across almost the whole molecule in the absence of antibody suggesting a very flexible structure. Exchange was slowed down across the central core of the molecule when bound to the antibody. This suggests that there are likely to be other sites of interaction with weaker binding in addition to the main one of 31-42.

Table 18 shows the percentage difference in deuteration levels comparing deuteration and exchange back to protons when bound to antibody 1 with deuteration in solution and exchange back to protons when bound to antibody. Differences of more than 10% when averaging the four time points were considered to be significant. Residue numbering is with the sequence shown in SEQ ID NO. 14.

TABLE 18

| Residue number | | Time point (s) | | | |
| --- | --- | --- | --- | --- | --- |
| start | end | 150 | 500 | 1500 | 5000 |
| 3 | 5 | 4 | 3 | -3 | 1 |
| 3 | 6 | 4 | 2 | 1 | -1 |
| 6 | 9 | 4 | -1 | -5 | -4 |
| 7 | 9 | 4 | 3 | -2 | -2 |
| 16 | 20 | 25 | 13 | 2 | -5 |
| 21 | 24 | 5 | 6 | 11 | 6 |
| 21 | 28 | 6 | 16 | 25 | 20 |
| 23 | 28 | 11 | 18 | 27 | 19 |
| 31 | 42 | 29 | 28 | 19 | 14 |
| 33 | 42 | 31 | 30 | 31 | 16 |
| 45 | 53 | 24 | 11 | 15 | 6 |
| 45 | 54 | 24 | 15 | 11 | 6 |
| 56 | 61 | 11 | 21 | 30 | 24 |
| 57 | 61 | 10 | 23 | 31 | 22 |
| 63 | 65 | 24 | 12 | -5 | -4 |
| 64 | 67 | 30 | 11 | -4 | -3 |
| 68 | 69 | 48 | 23 | 2 | -2 |
| 68 | 82 | 13 | 3 | -5 | -5 |
| 70 | 82 | 3 | 1 | -5 | -4 |
| 78 | 82 | 11 | 5 | -5 | -5 |

References

All references cited anywhere in this specification, including those cited anywhere above, are incorporated herein by reference in their entirety and for all purposes.

1 Ansel, K M. et al. Nature, 406: 309-314, 2000
2 Haan & Maggos (2004) BioCentury, 12(5): A1-A6
3 Koide et al. (1998) Journal of Molecular Biology, 284: 1141-1151.
4 Nygren et al. (1997) Current Opinion in Structural Biology, 7: 463-469
5 Wess, L. In: BioCentury, The Bernstein Report on BioBusiness, 12(42), A1-A7, 2004
6 Kabat, E. A. et al, Sequences of Proteins of Immunological Interest. $4^{th}$ Edition. US Department of Health and Human Services. 1987

7 Martin, A. C. R. Accessing the Kabat Antibody Sequence Database by Computer PROTEINS: Structure, Function and Genetics, 25 (1996), 130-133
8 Kabat, E. A. et al. (1991) Sequences of Proteins of Immunological Interest, 5th Edition. US Department of Health and Human Services, Public Service, NIH, Washington 9 Segal et al., PNAS, 71:4298-4302, 1974
10 Amit et al., Science, 233:747-753, 1986
11 Chothia et al., J. Mol. Biol., 196:901-917, 1987
12 Chothia et al., Nature, 342:877-883, 1989
13 Caton et al., J. Immunol., 144:1965-1968, 1990
14 Sharon et al., PNAS, 87:4814-4817, 1990
15 Sharon et al., J. Immunol., 144:4863-4869, 1990
16 Kabat et al., J. Immunol., 147:1709-1719, 1991
17 Holliger & Hudson, *Nature Biotechnology* 23(9):1126-1136 2005
18 Kontermann, R & Dubel, S, *Antibody Engineering*, Springer-Verlag New York, LLC; 2001, ISBN: 3540413545
19 Mendez, M. et al. (1997) Nature Genet, 15(2): 146-156
20 Knappik et al. J. Mol. Biol. (2000) 296, 57-86
21 Krebs et al. Journal of Immunological Methods 254 2001 67-84
22 Ward, E. S. et al., Nature 341, 544-546 (1989)
23 McCafferty et al (1990) Nature, 348, 552-554
24 Holt et al (2003) Trends in Biotechnology 21, 484-490
25 Bird et al, Science, 242, 423-426, 1988
26 Huston et al, PNAS USA, 85, 5879-5883, 1988
27 Holliger, P. et al, Proc. Natl. Acad. Sci. USA 90 6444-6448, 1993
28 Reiter, Y. et al, Nature Biotech, 14, 1239-1245, 1996
29 Hu, S. et al, Cancer Res., 56, 3055-3061, 1996
30 Holliger and Bohlen 1999 Cancer and metastasis rev. 18: 411-419
31 Holliger, P. and Winter G. Current Opinion Biotechnol 4, 446-449 1993
32 Glennie M J et al., 1987 J. Immunol. 139, 2367-2375
33 Repp R. et al., 1995 J. Hemat. 377-382
34 Staerz U. D. and Bevan M. J. 1986 PNAS 83
35 Suresh M. R. et al., 1986 Method Enzymol. 121: 210-228
36 Merchand et al., 1998 Nature Biotech. 16:677-681
37 Ridgeway, J. B. B. et al, Protein Eng., 9, 616-621, 1996
38 Harlow and Lane, Antibodies: A Laboratory Manual, Cold Spring Harbor Laboratory, Cold Spring Harbor N.Y., pp. 726, 1988
39 Köhler and Milstein, Nature, 256:495-497, 1975
40 Wold, et al. Multivariate data analysis in chemistry. Chemometrics-Mathematics and Statistics in Chemistry (Ed.: B. Kowalski), D. Reidel Publishing Company, Dordrecht, Holland, 1984 (ISBN 90-277-1846-6)
41 Norman et al. Applied Regression Analysis. Wiley-Interscience; 3rd edition (April 1998) ISBN: 0471170828
42 Kandel, Abraham & Backer, Eric. Computer-Assisted Reasoning in Cluster Analysis. Prentice Hall PTR, (May 11, 1995), ISBN: 0133418847
43 Krzanowski, Wojtek. Principles of Multivariate Analysis: A User's Perspective (Oxford Statistical Science Series, No 22 (Paper)). Oxford University Press; (December 2000), ISBN: 0198507089
44 Witten, Ian H. & Frank, Eibe. Data Mining: Practical Machine Learning Tools and Techniques with Java Implementations. Morgan Kaufmann; (Oct. 11, 1999), ISBN: 1558605525
45 Denison David G. T. (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002), ISBN: 0471490369
46 Ghose, Arup K. & Viswanadhan, Vellarkad N. Combinatorial Library Design and Evaluation Principles, Software, Tools, and Applications in Drug Discovery. ISBN: 0-8247-0487-8
47 Chothia C. et al. Journal Molecular Biology (1992) 227, 799-817
48 Al-Lazikani, et al. Journal Molecular Biology (1997) 273 (4), 927-948
49 Chothia, et al. Science, 223,755-758 (1986)
50 Whitelegg, N. R. u. and Rees, A. R (2000). Prot. Eng., 12, 815-824
51 Guex, N. and Peitsch, M. C. Electrophoresis (1997) 18, 2714-2723
52 Altschul et al. (1990) J. Mol. Biol. 215: 405-410
53 Pearson and Lipman (1988) PNAS USA 85: 2444-2448
54 Smith and Waterman (1981) J. Mol Biol. 147: 195-197
55 Voet & Voet, *Biochemistry*, 2nd Edition, (Wiley) 1995.
56 Gram et al., 1992, *Proc. Natl. Acad. Sci., USA*, 89:3576-3580
57 Barbas et al., 1994, *Proc. Natl. Acad. Sci., USA*, 91:3809-3813
58 Schier et al., 1996, *J. Mol. Biol.* 263:551-567
59 Marks et al *Bio/Technology*, 1992, 10:779-783
60 Kay, B. K., Winter, J., and McCafferty, J. (1996) Phage Display of Peptides and Proteins: A Laboratory Manual, San Diego: Academic Press
61 Hunter W. M. and Greenwood F. C. (1962) Nature 194:495
62 Plückthun, A. Bio/Technology 9: 545-551 (1991)
63 Chadd H E and Chamow S M (2001) Current Opinion in Biotechnology 12: 188-194
64 Andersen D C and Krummen L (2002) Current Opinion in Biotechnology 13: 117
65 Larrick J W and Thomas DW (2001) Current Opinion in Biotechnology 12:411-418
66 Sambrook and Russell, *Molecular Cloning: a Laboratory Manual:* 3rd edition, 2001, Cold Spring Harbor Laboratory Press
67 Ausubel et al. eds., *Short Protocols in Molecular Biology: A Compendium of Methods from Current Protocols in Molecular Biology*, John Wiley & Sons, 4th edition 1999
68 Shi, K. et al. J. Immunol, 166 : 650-655, 2001
69 Manzo, A. et al. Eur. J. Immunol, 35: 1347-1359, 2005
70 Kim, H-J. et al. J. Immunol, 162: 3053-3062, 1999
71 Carlson, H S. et al. Blood, 104: 3021-3027, 2004
72 Zheng, B. et al. Arthritis & Rheumatism, 52(2): 620-626, 2005
73 Mazezetti, I. et al. Arthritis & Rheumatism, 50(1): 112-122, 2004
74 Lisignoli, G. et al. J. Cell. Physiol, 206: 78-85, 2006
75 Lisignoli, G. et al. Experimental Gerontology, 39: 659-665, 2004
76 Bugatti, S. et al. Arthritis & Rheumatism, 52(11): 3448-3459, 2005
77 Schaerli, P. et al. J. Exp. Med, 192(11): 1553-1562, 2000
78 Breitfeld, D. et al. J. Exp. Med, 192(11): 1545-1551, 2000
79 Yu, P. et al. J. Immunol, 168: 5117-5123, 2002
80 Edwards, J C W. et al. Rheum. Dis. Clin. N. Am, 30: 393-403, 2004
81 Edwards, J C W, Cambridge, G. Nature. Rev. Immunol, 6: 394-403, 2006
82 Robinson, J. R. ed., Sustained and Controlled Release Drug Delivery Systems, Marcel Dekker, Inc., New York, 1978
83 Ledermann J. A. et al. (1991) Int. J. Cancer 47: 659-664

84 Bagshawe K. D. et al. (1991) Antibody, Immunoconjugates and Radiopharmaceuticals 4: 915-922
85 Bannister D., Wilson A., Prowse L., Walsh M., Holgate R., Jermutus J. and Wilkinson T. Biotechnology and Bioengineering, 94(5): 931-937
86 Dietz L. J., Dubrow R. S., Manian B. S. and Sizto. N. L., Cytometry 23:177-186, 1996
87 Foote, J and Winter G. J. Mol. Biol. 224(2): 487-499, 1992
88 Karlsson R., Michaelsson A. and Mattsson L. J. Immunol. Methods, 145(102): 229-240, 1991
89 Hutchings, C. Generation of Naive Human Antibody Libraries, in Antibody Engineering, R. Kontermann and S. Dubel, Editors. 2001, Springer Laboratory Manuals, Berlin. p. 93
90 Mach et al. Anal. Biochem. 200(1): 20-26, 1992
100 Mellentin-Michelotti J., Evangelista, L., Swartzman E. E., Miraglia, S. J., Werner W. and Yuan P.-M Anal. Biochem 272: 182-190, 1999
101 Miraglia S., Swartzman E. E., Mellentin-Michelotti J., Evangelista, L., Smith C., Gunawan I., Lohman K., Goldberg E. M., Manian B. and Yuan P.-M. J Biomol. Screening 4:193-204, 1999
102 Osbourn, J K. et al. Immunotechnology, 2(3):181-96, 1996
103 Persic, L. et al. Gene. 187(1): 9-18, 1997
104 Swartzman E. E., Miraglia S. J., Mellentin-Michelotti J., Evangelista L. and Yuan P-M. Anal. Biochem 271: 143-151, 1999
105 Tomlinson, I., VBASE. MRC Centre of Protein Engineering, Cambridge, UK, 1997
106 Vaughan, T J. et al. Nature Biotechnology 14(3):309-14, 1996
107 Zlotnik, A. and Yoshie, O. Immunity 12:121-7, 2000

The invention claimed is:

1. An isolated antibody for CXCL13, wherein the antibody inhibits binding of human CXCL13 to human CXCR5 and wherein the antibody comprises a set of antibody CDRs: HCDR1, HCDR2, HCDR3, LCDR1, LCDR2 and LCDR3, defined wherein: HCDR1 has amino acid sequence SEQ ID NO: 3; HCDR2 has amino acid sequence SEQ ID NO: 4; HCDR3 has amino acid sequence SEQ ID NO: 5; LCDR1 has amino acid sequence SEQ ID NO: 8; LCDR2 has amino acid sequence SEQ ID NO: 9; and LCDR3 has amino acid sequence SEQ ID NO: 10.

2. The antibody according to claim 1, wherein the antibody is an scFv.

3. The antibody according to claim 1, wherein the antibody is an IgG1.

4. The antibody according to claim 1, wherein the antibody VH domain amino acid sequence is SEQ ID NO: 2.

5. The antibody according to claim 1, wherein the VL domain amino acid sequence is SEQ ID NO: 7.

6. The antibody according to claim 1, wherein the antibody VH domain amino acid sequence is SEQ ID NO: 2; and the antibody VL domain amino acid sequence is SEQ ID NO: 7.

7. A composition comprising the isolated antibody according to claim 1 and a pharmaceutically acceptable excipient.

8. An isolated nucleic acid molecule comprising a nucleotide encoding the antibody according to claim 1.

9. A host cell in vitro transformed with the isolated nucleic acid molecule according to claim 8.

10. A method of producing an antibody comprising culturing host cells according to claim 9 under conditions for production of the antibody.

11. The method according to claim 10, further comprising isolating and/or purifying the antibody.

12. The method according to claim 11, further comprising formulating the antibody into a composition comprising at least one additional component.

* * * * *

SEQUENCE LISTING

<160> NUMBER OF SEQ ID NOS: 20

<210> SEQ ID NO 1
<211> LENGTH: 357
<212> TYPE: DNA
<213> ORGANISM: Homo sapiens
<220> FEATURE:
<223> OTHER INFORMATION: Antibody1

<400> SEQUENCE: 1
gaggtgcagc tgctggagtc tgggggaggc ttggtgcagc caggggggtc cctgagactc      60
tcctgtgcag cctctggatt cacctttggt aattcttgga tgagttgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgcg agctgaggac acggctgtgt attactgtac gagagatctt     300
ccgggtatag cagtggctgg ttactggggc cagggcaccc tggtcaccgt ctcgagt       357

<210> SEQ ID NO 2
<211> LENGTH: 119
<212> TYPE: PRT
<213> ORGANISM: Homo sapiens
<220> FEATURE:
<223> OTHER INFORMATION: Antibody1

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Ser
            20                  25                  30

Trp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp Leu Pro Gly Ile Ala Val Ala Gly Tyr Trp Gly Gln Gly
            100                 105                 110

Thr Leu Val Thr Val Ser Ser

<210> SEQ ID NO 3
<211> LENGTH: 5
<212> TYPE: PRT
<213> ORGANISM: Homo sapiens
<220> FEATURE:
<223> OTHER INFORMATION: Antibody1

<400> SEQUENCE: 3

Asn Ser Trp Met Ser
1               5

<210> SEQ ID NO 4
<211> LENGTH: 17
<212> TYPE: PRT
<213> ORGANISM: Homo sapiens
<220> FEATURE:
<223> OTHER INFORMATION: Antibody1

<400> SEQUENCE: 4

Ala Ile Ser Gly Ser Gly Gly Ser Thr Tyr Tyr Ala Asp Ser Val Lys
1               5                   10                  15

Gly

<210> SEQ ID NO 5
<211> LENGTH: 10
<212> TYPE: PRT
<213> ORGANISM: Homo sapiens
<220> FEATURE:
<223> OTHER INFORMATION: Antibody1

<400> SEQUENCE: 5

Asp Leu Pro Gly Ile Ala Val Ala Gly Tyr
1               5                   10

<210> SEQ ID NO 6
<211> LENGTH: 324
<212> TYPE: DNA
<213> ORGANISM: Homo sapiens
<220> FEATURE:
<223> OTHER INFORMATION: Antibody1

<400> SEQUENCE: 6
gacacccaga tgacccagtc tccttccacc ctgtctgcat ctgttggaga cagagtcacc     60
atcacctgcc gggccagtga gggtatttat cactggttgg cctggtatca gcagaagcca    120
gggaaagccc ctaaactcct gatctataag gcctctagtt tagccagtgg ggtcccatca    180
aggttcagcg gcagtggatc tgggacagag ttcactctca ccatcagcag cctgcagcct    240
gatgattttg caacttatta ctgccaacaa tatagtaatt atccgctcac tttcggcgga    300
gggaccaagc tggagatcaa acgt                                           324

<210> SEQ ID NO 7
<211> LENGTH: 108
<212> TYPE: PRT
<213> ORGANISM: Homo sapiens
<220> FEATURE:
<223> OTHER INFORMATION: Antibody1

<400> SEQUENCE: 7

Asp Thr Gln Met Thr Gln Ser Pro Ser Thr Leu Ser Ala Ser Val Gly
1               5                   10                  15

Asp Arg Val Thr Ile Thr Cys Arg Ala Ser Glu Gly Ile Tyr His Trp
            20                  25                  30

```
Leu Ala Trp Tyr Gln Gln Lys Pro Gly Lys Ala Pro Lys Leu Leu Ile
            35                  40                  45

Tyr Lys Ala Ser Ser Leu Ala Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Ser Asn Tyr Pro Leu
                 85                  90                  95

Thr Phe Gly Gly Gly Thr Lys Leu Glu Ile Lys Arg
            100                 105
```

<210> SEQ ID NO 8
<211> LENGTH: 11
<212> TYPE: PRT
<213> ORGANISM: Homo sapiens
<220> FEATURE:
<223> OTHER INFORMATION: Antibody1

<400> SEQUENCE: 8

```
Arg Ala Ser Glu Gly Ile Tyr His Trp Leu Ala
 1               5                  10
```

<210> SEQ ID NO 9
<211> LENGTH: 7
<212> TYPE: PRT
<213> ORGANISM: Homo sapiens
<220> FEATURE:
<223> OTHER INFORMATION: Antibody1

<400> SEQUENCE: 9

```
Lys Ala Ser Ser Leu Ala Ser
 1               5
```

<210> SEQ ID NO 10
<211> LENGTH: 9
<212> TYPE: PRT
<213> ORGANISM: Homo sapiens
<220> FEATURE:
<223> OTHER INFORMATION: Antibody1

<400> SEQUENCE: 10

```
Gln Gln Tyr Ser Asn Tyr Pro Leu Thr
 1               5
```

<210> SEQ ID NO 11
<211> LENGTH: 242
<212> TYPE: PRT
<213> ORGANISM: Homo sapiens
<220> FEATURE:
<223> OTHER INFORMATION: Antibody 1 scFv amino acid sequence (VH
      followed by VL with linker sequence)

<400> SEQUENCE: 11

```
Gln Val Gln Leu Val Glu Ser Gly Gly Gly Leu Val Gln Pro Gly Arg
 1               5                  10                  15

Ser Leu Arg Leu Ser Cys Val Gly Ser Gly Phe Thr Phe Gly Asn Ser
             20                  25                  30

Trp Met Ser Trp Val Arg His Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Gly Ala Glu Asp Thr Ala Val Tyr Tyr Cys
                85                  90                  95

Thr Arg Asp Leu Pro Gly Ile Ala Val Ala Gly Tyr Trp Gly Arg Gly
            100                 105                 110

Thr Leu Val Thr Val Ser Ser Gly Gly Gly Gly Ser Gly Gly Gly Gly
            115                 120                 125

Ser Gly Gly Gly Gly Ser Asp Thr Gln Met Thr Gln Ser Pro Ser Thr
130                 135                 140

Leu Ser Ala Ser Ile Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Ala
            180                 185                 190

Pro Ser Arg Phe Ser Gly Ser Gly Ser Gly Thr Asp Phe Thr Leu Thr
            195                 200                 205

Ile Ser Ser Leu Gln Pro Asp Asp Phe Ala Thr Tyr Tyr Cys Gln Gln
            210                 215                 220

Tyr Ser Asn Tyr Pro Leu Thr Phe Gly Gly Gly Thr Lys Leu Glu Ile
225                 230                 235                 240

Lys Arg

<210> SEQ ID NO 12
<211> LENGTH: 109
<212> TYPE: PRT
<213> ORGANISM: Homo sapiens
<220> FEATURE:
<223> OTHER INFORMATION: Full length human CXCL13 amino acid sequence

<400> SEQUENCE: 12

Met Lys Phe Ile Ser Thr Ser Leu Leu Leu Met Leu Leu Val Ser Ser
1               5                   10                  15

Leu Ser Pro Val Gln Gly Val Leu Glu Val Tyr Tyr Thr Ser Leu Arg
            20                  25                  30

Cys Arg Cys Val Gln Glu Ser Ser Val Phe Ile Pro Arg Arg Phe Ile
            35                  40                  45

Asp Arg Ile Gln Ile Leu Pro Arg Gly Asn Gly Cys Pro Arg Lys Glu
50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
            100                 105

<210> SEQ ID NO 13
<211> LENGTH: 87
<212> TYPE: PRT
<213> ORGANISM: Homo sapiens
<220> FEATURE:
<223> OTHER INFORMATION: Mature human CXCL13 amino acid sequence

<400> SEQUENCE: 13

Val Leu Glu Val Tyr Tyr Thr Ser Leu Arg Cys Arg Cys Val Gln Glu
1               5                   10                  15

Ser Ser Val Phe Ile Pro Arg Arg Phe Ile Asp Arg Ile Gln Ile Leu
            20                  25                  30
```

```
Pro Arg Gly Asn Gly Cys Pro Arg Lys Glu Ile Ile Val Trp Lys Lys
            35                  40                  45

Asn Lys Ser Ile Val Cys Val Asp Pro Gln Ala Glu Trp Ile Gln Arg
     50                  55                  60

Met Met Glu Val Leu Arg Lys Arg Ser Ser Thr Leu Pro Val Pro
 65              70                  75                  80

Val Phe Lys Arg Lys Ile Pro
                85

<210> SEQ ID NO 14
<211> LENGTH: 82
<212> TYPE: PRT
<213> ORGANISM: Homo sapiens
<220> FEATURE:
<223> OTHER INFORMATION: Mature human CXCL13 amino acid sequence with C
      terminal truncation

<400> SEQUENCE: 14

Val Leu Glu Val Tyr Tyr Thr Ser Leu Arg Cys Arg Cys Val Gln Glu
 1               5                  10                  15

Ser Ser Val Phe Ile Pro Arg Arg Phe Ile Asp Arg Ile Gln Ile Leu
            20                  25                  30

Pro Arg Gly Asn Gly Cys Pro Arg Lys Glu Ile Ile Val Trp Lys Lys
            35                  40                  45

Asn Lys Ser Ile Val Cys Val Asp Pro Gln Ala Glu Trp Ile Gln Arg
     50                  55                  60

Met Met Glu Val Leu Arg Lys Arg Ser Ser Thr Leu Pro Val Pro
 65              70                  75                  80

Val Phe

<210> SEQ ID NO 15
<211> LENGTH: 87
<212> TYPE: PRT
<213> ORGANISM: Macaca fascicularis
<220> FEATURE:
<223> OTHER INFORMATION: Mature cynomolgus CXCL13 amino acid sequence

<400> SEQUENCE: 15

Val Leu Glu Val Tyr Tyr Thr His Leu Arg Cys Arg Cys Val Gln Glu
 1               5                  10                  15

Ser Ser Val Phe Ile Pro Arg Arg Phe Ile Asp Arg Ile Gln Ile Ser
            20                  25                  30

Pro Arg Gly Asn Gly Cys Pro Arg Lys Glu Ile Ile Val Trp Lys Lys
            35                  40                  45

Asn Lys Ser Val Val Cys Val Asp Pro Gln Ala Glu Trp Ile Gln Arg
     50                  55                  60

Ile Met Glu Met Leu Arg Lys Lys Ser Ser Ser Thr Pro Pro Val Pro
 65              70                  75                  80

Val Phe Lys Arg Lys Ile Pro
                85

<210> SEQ ID NO 16
<211> LENGTH: 82
<212> TYPE: PRT
<213> ORGANISM: Macaca fascicularis
<220> FEATURE:
<223> OTHER INFORMATION: Mature cynomolgus CXCL13 amino acid sequence
      with C terminal truncation

<400> SEQUENCE: 16

Val Leu Glu Val Tyr Tyr Thr His Leu Arg Cys Arg Cys Val Gln Glu
```

-continued

```
              1               5              10              15
Ser Ser Val Phe Ile Pro Arg Arg Phe Ile Asp Arg Ile Gln Ile Ser
                20                  25                  30

Pro Arg Gly Asn Gly Cys Pro Arg Lys Glu Ile Ile Val Trp Lys Lys
            35                  40                  45

Asn Lys Ser Val Val Cys Val Asp Pro Gln Ala Glu Trp Ile Gln Arg
        50                  55                  60

Ile Met Glu Met Leu Arg Lys Lys Ser Ser Thr Pro Pro Val Pro
65                  70                  75                  80

Val Phe
```

<210> SEQ ID NO 17
<211> LENGTH: 372
<212> TYPE: PRT
<213> ORGANISM: Homo sapiens
<220> FEATURE:
<223> OTHER INFORMATION: Human CXCR5 isoform 1 amino acid sequence

<400> SEQUENCE: 17

```
Met Asn Tyr Pro Leu Thr Leu Glu Met Asp Leu Glu Asn Leu Glu Asp
1               5                  10                  15

Leu Phe Trp Glu Leu Asp Arg Leu Asp Asn Tyr Asn Asp Thr Ser Leu
                20                  25                  30

Val Glu Asn His Leu Cys Pro Ala Thr Glu Gly Pro Leu Met Ala Ser
            35                  40                  45

Phe Lys Ala Val Phe Val Pro Val Ala Tyr Ser Leu Ile Phe Leu Leu
        50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
            180                 185                 190

Gly His His Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
    210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Ala Arg Leu Lys
        275                 280                 285
```

```
Ala Val Asp Asn Thr Cys Lys Leu Asn Gly Ser Leu Pro Val Ala Ile
            290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
            340                 345                 350

Pro Ser Trp Arg Arg Ser Ser Leu Ser Glu Ser Glu Asn Ala Thr Ser
        355                 360                 365

Leu Thr Thr Phe
    370

<210> SEQ ID NO 18
<211> LENGTH: 327
<212> TYPE: PRT
<213> ORGANISM: Homo sapiens
<220> FEATURE:
<223> OTHER INFORMATION: Human CXCR5 isoform 2 amino acid sequence

<400> SEQUENCE: 18

Met Ala Ser Phe Lys Ala Val Phe Val Pro Val Ala Tyr Ser Leu Ile
1               5                   10                  15

Phe Leu Leu Gly Val Ile Gly Asn Val Leu Val Leu Val Ile Leu Glu
            20                  25                  30

Arg His Arg Gln Thr Arg Ser Ser Thr Glu Thr Phe Leu Phe His Leu
        35                  40                  45

Ala Val Ala Asp Leu Leu Leu Val Phe Ile Leu Pro Phe Ala Val Ala
    50                  55                  60

Glu Gly Ser Val Gly Trp Val Leu Gly Thr Phe Leu Cys Lys Thr Val
65                  70                  75                  80

Ile Ala Leu His Lys Val Asn Phe Tyr Cys Ser Ser Leu Leu Leu Ala
                85                  90                  95

Cys Ile Ala Val Asp Arg Tyr Leu Ala Ile Val His Ala Val His Ala
            100                 105                 110

Tyr Arg His Arg Arg Leu Leu Ser Ile His Ile Thr Cys Gly Thr Ile
        115                 120                 125

Trp Leu Val Gly Phe Leu Leu Ala Leu Pro Glu Ile Leu Phe Ala Lys
    130                 135                 140

Val Ser Gln Gly His His Asn Asn Ser Leu Pro Arg Cys Thr Phe Ser
145                 150                 155                 160

Gln Glu Asn Gln Ala Glu Thr His Ala Trp Phe Thr Ser Arg Phe Leu
                165                 170                 175

Tyr His Val Ala Gly Phe Leu Leu Pro Met Leu Val Met Gly Trp Cys
            180                 185                 190

Tyr Val Gly Val Val His Arg Leu Arg Gln Ala Gln Arg Arg Pro Gln
        195                 200                 205

Arg Gln Lys Ala Val Arg Val Ala Ile Leu Val Thr Ser Ile Phe Phe
    210                 215                 220

Leu Cys Trp Ser Pro Tyr His Ile Val Ile Phe Leu Asp Thr Leu Ala
225                 230                 235                 240

Arg Leu Lys Ala Val Asp Asn Thr Cys Lys Leu Asn Gly Ser Leu Pro
                245                 250                 255

Val Ala Ile Thr Met Cys Glu Phe Leu Gly Leu Ala His Cys Cys Leu
            260                 265                 270

Asn Pro Met Leu Tyr Thr Phe Ala Gly Val Lys Phe Arg Ser Asp Leu
```

```
                    275                 280                 285
Ser Arg Leu Leu Thr Lys Leu Gly Cys Thr Gly Pro Ala Ser Leu Cys
290                 295                 300

Gln Leu Phe Pro Ser Trp Arg Arg Ser Ser Leu Ser Glu Ser Glu Asn
305                 310                 315                 320

Ala Thr Ser Leu Thr Thr Phe
                325

<210> SEQ ID NO 19
<211> LENGTH: 353
<212> TYPE: PRT
<213> ORGANISM: Homo sapiens
<220> FEATURE:
<223> OTHER INFORMATION: G protein Gqi5 amino acid sequence

<400> SEQUENCE: 19

Met Ala Cys Cys Leu Ser Glu Glu Ala Lys Glu Ala Arg Arg Ile Asn
1               5                   10                  15

Asp Glu Ile Glu Arg Gln Leu Arg Arg Asp Lys Arg Asp Ala Arg Arg
            20                  25                  30

Glu Leu Lys Leu Leu Leu Gly Thr Gly Glu Ser Gly Lys Ser Thr
        35                  40                  45

Phe Ile Lys Gln Met Arg Ile Ile His Gly Ser Gly Tyr Ser Asp Glu
    50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
            100                 105                 110

Glu Lys Val Ser Ala Phe Asp Val Pro Asp Tyr Ala Ala Ile Lys Ser
        115                 120                 125

Leu Trp Asn Asp Pro Gly Ile Gln Glu Cys Tyr Asp Arg Arg Arg Glu
    130                 135                 140

Tyr Gln Leu Ser Asp Ser Thr Lys Tyr Tyr Leu Asn Asp Leu Asp Arg
145                 150                 155                 160

Val Ala Asp Pro Ser Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
            180                 185                 190

Val Ile Phe Arg Met Val Asp Val Gly Gly Gln Arg Ser Glu Arg Arg
        195                 200                 205

Lys Trp Ile His Cys Phe Glu Asn Val Thr Ser Ile Met Phe Leu Val
    210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Gln Arg Asp Ala Gln Ala Ala Arg Glu Phe Ile Leu
    290                 295                 300

Lys Met Phe Val Asp Leu Asn Pro Asp Ser Asp Lys Ile Ile Tyr Ser
305                 310                 315                 320
```

```
His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Asp Gly Gly Leu
            340                 345                 350

Phe

<210> SEQ ID NO 20
<211> LENGTH: 12
<212> TYPE: PRT
<213> ORGANISM: Homo sapiens
<220> FEATURE:
<223> OTHER INFORMATION: Human CXCL-13 peptide

<400> SEQUENCE: 20

Ile Leu Pro Arg Gly Asn Gly Cys Pro Arg Lys Glu
1               5                   10
```